US011446256B1

(12) United States Patent
Spanjer et al.

(10) Patent No.: US 11,446,256 B1
(45) Date of Patent: Sep. 20, 2022

(54) AQUEOUS WOUND HEALING FORMULATION

(71) Applicant: Advantice Health, LLC, Cedar Knolls, NJ (US)

(72) Inventors: Hellen Spanjer, Cedar Knolls, NJ (US); Kathryn Jill Rivera, Cedar Knolls, NJ (US); Stephen Maida, Cedar Knolls, NJ (US); Joseph Librizzi, Hillsborough, NJ (US); Anthony D'Ovidio, Hillsborough, NJ (US)

(73) Assignee: ADVANTICE HEALTH, LLC, Cedar Knolls, NJ (US)

( * ) Notice: Subject to any disclaimer, the term of this patent is extended or adjusted under 35 U.S.C. 154(b) by 0 days.

(21) Appl. No.: 17/407,354

(22) Filed: Aug. 20, 2021

(51) Int. Cl.
| | |
|---|---|
| *A61P 17/02* | (2006.01) |
| *A61K 9/70* | (2006.01) |
| *A61K 47/34* | (2017.01) |
| *A61K 31/14* | (2006.01) |
| *A61K 31/155* | (2006.01) |
| *A61K 31/055* | (2006.01) |
| *A61K 31/167* | (2006.01) |
| *A61K 31/245* | (2006.01) |
| *A61K 31/47* | (2006.01) |
| *A61K 36/886* | (2006.01) |
| *A61K 36/61* | (2006.01) |
| *A61K 36/28* | (2006.01) |
| *A61K 36/53* | (2006.01) |
| *A61K 36/288* | (2006.01) |
| *A61K 36/48* | (2006.01) |
| *A61K 31/573* | (2006.01) |
| *A61K 47/36* | (2006.01) |
| *A61K 47/32* | (2006.01) |
| *A61K 9/00* | (2006.01) |

(52) U.S. Cl.
CPC .......... *A61K 9/7015* (2013.01); *A61K 9/0014* (2013.01); *A61K 31/055* (2013.01); *A61K 31/14* (2013.01); *A61K 31/155* (2013.01); *A61K 31/167* (2013.01); *A61K 31/245* (2013.01); *A61K 31/47* (2013.01); *A61K 31/573* (2013.01); *A61K 36/28* (2013.01); *A61K 36/288* (2013.01); *A61K 36/48* (2013.01); *A61K 36/53* (2013.01); *A61K 36/61* (2013.01); *A61K 36/886* (2013.01); *A61K 47/32* (2013.01); *A61K 47/34* (2013.01); *A61K 47/36* (2013.01); *A61P 17/02* (2018.01)

(58) Field of Classification Search
CPC combination set(s) only.
See application file for complete search history.

(56) References Cited

U.S. PATENT DOCUMENTS

| | | | | |
|---|---|---|---|---|
| 3,214,338 | A | * | 10/1965 | Joseph ................. A61K 9/7015 514/772.4 |
| 3,547,950 | A | | 12/1970 | Gander |
| 4,885,161 | A | | 12/1989 | Cornell |
| 5,135,755 | A | | 8/1992 | Czech et al. |
| 5,456,745 | A | | 10/1995 | Roreger et al. |
| 5,902,600 | A | | 5/1999 | Moller et al. |
| 6,224,622 | B1 | | 5/2001 | Kotzev |
| 6,386,203 | B1 | | 5/2002 | Hammerslag |
| 7,918,621 | B2 | | 4/2011 | Battisti |
| 8,217,110 | B2 | | 7/2012 | Melancon |
| 2006/0173111 | A1 | | 8/2006 | Karpowicz |
| 2009/0192475 | A1 | | 7/2009 | Siegel |
| 2011/0045056 | A1 | | 2/2011 | Munro |
| 2019/0247352 | A1 | * | 8/2019 | Zheng ..................... A61P 17/18 |

FOREIGN PATENT DOCUMENTS

| | | | |
|---|---|---|---|
| CH | 530795 | A | 11/1972 |
| CN | 1660449 | A | 8/2005 |
| CN | 103463669 | A | 12/2013 |
| CN | 105797202 | A | 7/2016 |
| CN | 106474536 | A | 3/2017 |
| CN | 106474537 | A | 3/2017 |
| CN | 109568652 | A | 4/2019 |
| CN | 109836533 | A | 6/2019 |
| CN | 110251720 | A | 9/2019 |
| CN | 111195369 | A | 5/2020 |
| CN | 112076342 | A | 12/2020 |
| EP | 2196225 | A2 | 6/2010 |
| FR | 2144587 | A1 | 2/1973 |
| GB | 1041097 | A | 9/1966 |
| GB | 1108941 | A | 4/1968 |
| GB | 1292953 | A | 10/1972 |
| GB | 1465190 | A | 2/1977 |
| KR | 2011109250 | A | * 10/2011 |
| WO | 91/05574 | A1 | 5/1991 |

(Continued)

OTHER PUBLICATIONS

Elegbede et al., "Effect of Fermented and Green Aspalathus linearis Extract Loaded Hydrogel on Surgical Wound Healing in Sprague Dawley Rats," Wound Medicine 29:100186 (2020).

Yan et al.,"Thermoresponsive in Situ Forming Hydrogel with Sol-Gel Irreversibility for Effective Methicillin-Resistant *Staphylococcus aureus* Infected Wound Healing," ACS Nano 13(9):10074-10084 (2019).

(Continued)

*Primary Examiner* — Qiuwen Mi
(74) *Attorney, Agent, or Firm* — Troutman Pepper Hamilton Sanders LLP (Rochester)

(57) ABSTRACT

The present invention relates to a water resistant wound cover with high comfort and good air permeability. In particular, the present invention relates to an aqueous wound healing formulation comprising a water-soluble or a water-dispersible polymeric material that does not sting when applied to a minor injury to the skin.

24 Claims, No Drawings

(56) References Cited

FOREIGN PATENT DOCUMENTS

| | | |
|---|---|---|
| WO | 93/06802 A1 | 4/1993 |
| WO | 95/07719 A1 | 3/1995 |
| WO | 99/17814 A1 | 4/1999 |
| WO | 99/22934 A1 | 5/1999 |
| WO | 2001/037890 A1 | 5/2001 |
| WO | 2001/045762 A2 | 6/2001 |
| WO | 31/96422 A1 | 12/2001 |
| WO | 2002/022182 A1 | 3/2002 |
| WO | 2002/026845 A1 | 4/2002 |
| WO | 2003/063923 A1 | 8/2003 |
| WO | 2003/075886 A1 | 9/2003 |
| WO | 2003/075968 A2 | 9/2003 |
| WO | 2008/048468 A1 | 4/2008 |
| WO | 2011/013546 A1 | 2/2011 |
| WO | 2012/039887 A1 | 3/2012 |
| WO | 2012/136934 A2 | 10/2012 |
| WO | 2017/069079 A1 | 4/2017 |
| WO | 2020/110325 A1 | 6/2020 |

OTHER PUBLICATIONS

Xue et al., "Quaternized Chitosan-Matrigel-polyacrylamide Hydrogels as Wound Dressing for Wound Repair and Regeneration," Carbohydrate Polymers 226:115302 (2019).

Zubris et al., "Polymeric Quaternary Ammonium Compounds: Versatile Antimicrobial Materials," Current Topics in Medicinal Chemistry 17(3):305-318 (2017).

KeriCure's Natural Seal Liquid Bandage (2017).

Hunter et al., "Hydrogel Wound Dressings: Where Do We Stand in 2003?," Ostomy/Wound Management 49 (10):52-57 (2003).

S. Misterka, "Clinical Evaluation of Hydrogel-type Dressing Materials After Their 8-year Use," Polimery w Medycynie 21(1-2):23-30 (1991) (abstract only).

* cited by examiner

AQUEOUS WOUND HEALING FORMULATION

TECHNICAL FIELD OF THE INVENTION

The present invention relates to a water resistant wound cover with high comfort and good air permeability. In particular, the present invention relates to an aqueous wound healing formulation comprising a water-soluble or a water-dispersible polymeric material that does not sting when applied to a minor injury to the skin.

BACKGROUND OF THE INVENTION

Minor injuries to the skin are typically treated by applying a wound cover, such as a plaster, bandage or dressing, to the point of injury. Such treatment aims to stop the bleeding, bring the wound edges together to promote healing, and prevent contamination of the wound to reduce risk of infection. Conventional wound covers are typically selected from textile bandages and adhesive bandages.

Textile bandages are often used to hold a dressing in place or in the elastic variation to reduce swelling. The most common type of bandage is the gauze bandage, which is a woven material with an absorbent barrier to prevent adhesion to the wound. Textile bandages are mainly used in the case of larger and more severe injuries to the skin, joints, or ligaments.

Conversely, adhesive bandages (or plasters) are commonly used to protect minor injuries to the skin from abrasion, dirt and contamination. Adhesive bandages comprise a flexible sheet of material with a single sticky side on which is positioned a smaller non-sticky and absorbent pad that is placed against the wound. The adhesive sheet can be made from a woven fabric, plastics, such as PVC, polyethylene or polyurethane, or latex. In many instances, the adhesive is an acrylate, such as a methacrylate or an epoxy diacrylate. The absorbent pad is most often made from cotton, sometimes covered with a thin coating to prevent it from sticking to the wound.

Unfortunately, these conventional wound covers come with some drawbacks, such as the need for keeping the textile or adhesive bandages sterile during storage and upon application. This requirement often conflicts with the need for the wound covers to be breathable and therefore designed to be porous and permeable. Moreover, these conventional wound covers tend to accumulate dirt in use or suffer from the inability to stay in place over flexing joints, such as knees, elbows and knuckles, leaving openings that increase the risk of infection at the site of injury. Therefore, to maintain a sufficient level of hygiene at the wound, frequent changing of the wound cover is therefore required, which ultimately present a risk of a secondary infection. Consequently, there is a difficult balance to be struck between sanitation at the injury site and the requirement for breathability of the skin. Other disadvantages of textile based wound covers include difficulties in making the wound cover stick in positions that are not easily accessible, such as in between fingers and toes, pain associated with contacting the site of injury with a textile material, and frequent occurrence of allergies of patients to materials in the wound covers, especially latex and some adhesives.

Liquid bandages may remedy some of the deficiencies associated with conventional wound covers. Available liquid bandages comprise mixtures of a polymer dissolved in an organic solvent. Upon application to the skin the solvent evaporates and leaves a polymeric film covering a minor injury on the skin. Liquid bandages may include polymers such as ethyl cellulose, nitrocellulose, methacrylates, cyanoacrylates and siloxane. Especially cyanoacrylates, such as methyl 2-cyanoacrylate (MCA), ethyl 2-cyanoacrylate (ECA), n-butyl cyanoacrylate (n-BCA), octyl cyanoacrylate, and 2-octyl cyanoacrylate, are fast-acting adhesives frequently used in liquid bandages. These polymers are known for their adhesive strength and are common components in superglues. Implementation of cyanoacrylates in liquid bandages have thus encouraged surgical use in which liquid bandages in some cases can substitute the need for sutures and staples.

Thus, amongst other things, liquid formulations remove the need for storing a solid material under sterile conditions and overcome the issue of poor accessibility of classic strip bandages. However, available liquid bandages sting when applied to the site of injury due to the presence of an organic solvent, the film-forming polymer, or a combination thereof. Moreover, the use of certain polymers may be toxic and unsuitable for children or frequent use in general.

Hence, it would be advantageous to provide a wound cover that is easy to use, has excellent performance, and does not sting or irritate the skin upon application. Particularly, it would be advantageous to provide a liquid bandage formulation that does not rely on organic solvents and/or toxic polymers.

SUMMARY OF THE INVENTION

First line of treatment of minor injuries to the skin is typically wound covers that solves the immediate need to stop bleeding, prevent infection and initiate the healing process. Conventional wound covers include textile bandages and adhesive bandages. Liquid bandages on the other hand are favorable from a patient point of view due to the ease of application and aesthetically appealing appearance. However, the presence of organic solvents and toxic polymers in most liquid bandages can cause irritation to the skin and bring about an unpleasant stinging sensation and harsh scent. Thus, there is an unmet need for a liquid wound healing formulation which provides the benefits of known liquid bandages but without adverse effects, such as irritation of the skin and any uncomfortable sensations.

The present invention relates to an aqueous wound healing formulation and a method of treatment of a minor skin wound. The formulation is based on a water-soluble or a water-dispersible polymeric material which adheres to the skin and establish conditions favorable for an efficient healing process. By obviating the need for organic solvents and toxic polymers, the aqueous wound healing formulation provide excellent performance along with improved comfort to treat a variety of minor injuries to the skin, such as abrasions, cuts, mild burns and other superficial wounds.

Thus, an object of the present invention relates to the provision of aqueous wound healing formulation which does not irritate the skin or sting upon application.

In particular, it is an object of the present invention to provide a method of treatment of minor skin wounds that is especially suited for children and individuals that reacts adversely to other liquid bandages.

Thus, an aspect of the present invention relates to a method of treatment of a minor injury to the skin, which method comprises topically applying to said injured area an aqueous formulation comprising a water-soluble or a water-dispersible polymeric material, which polymeric material is capable of:
  (i) adhering to the skin; and
  (ii) acting as a barrier to moisture but not to oxygen,
to cover said injured area, and then allowing water within the aqueous formulation to evaporate to leave a film comprising said polymeric material that covers said injured area, to treat said minor injury.

Another aspect of the present invention relates to an aqueous wound healing formulation comprising:
  (i) a water-soluble or a water-dispersible polymeric material comprising:
    a first polymer comprising a vinyl polymer, and
    a second polymer comprising an acrylic polymer;
  (ii) optionally, one or more thickening agents; and
  (iii) optionally, one or more preservative agents.

Yet another aspect of the present invention relates to a container comprising an aqueous wound healing formulation as described herein.

Still another aspect of the present invention relates to a method for producing an aqueous wound healing formulation as described herein, said method comprising the steps of:
  (i) providing a mixing container comprising an aqueous solvent,
  (ii) adding the first polymer to said mixing container under stirring, and
  (iii) adding the second polymer to said mixing container under stirring.

A further aspect of the present invention relates to an aqueous wound healing formulation as described herein for use as a medicament.

A still further aspect of the present invention relates to an aqueous wound healing formulation as described herein for use in the treatment of a minor injury to the skin.

An even further aspect of the present invention relates to the use of a water-soluble or a water-dispersible polymeric material comprising a first polymer which is a vinyl polymer, and a second polymer which is an acrylic polymer, for preparation of an aqueous wound healing formulation.

An additional aspect of the present invention relates to a kit-of-parts comprising:
  (i) an aqueous wound healing formulation as described herein and optionally a means for applying the aqueous wound healing formulation to the skin; or
  (ii) a container as described herein; and
  (iii) instructions for use.

The present invention will in the following be described in more detail.

DETAILED DESCRIPTION OF THE INVENTION

Definitions

Prior to outlining the present invention in more details, a set of terms and conventions is first defined:

Aqueous Formulation

In the present context, the term "aqueous formulation" refers to a liquid composition consisting primarily of water. Thus, the aqueous formulation comprises more than 50 wt % water, such as at least 55 wt % water, such as at least 60 wt % water, preferably at least 65 wt % water. In some formulations the content of water may be even greater, such as about 65 wt % to about 90 wt % water.

The aqueous formulations disclosed herein are suitable for treatment, prevention, or inhibition of minor injuries to the skin and are therefore also referred to as aqueous wound healing formulations.

Aqueous Wound Healing Formulation

In the present context, the term "aqueous wound healing formulation" refers to a composition as defined above that can be used to treat, prevent, or inhibit minor injuries. When applied to the skin it leaves a protecting film that forms a barrier to water and environmental irritants, such as wind, dry air, friction, bacteria, or germs, but at the same time is breathable. These characteristics establish conditions at the minor injury, including moisture level, that are favorable for an efficient healing process.

In this respect, the aqueous wound healing formulations disclosed herein may be sterile or, more preferably, non-sterile, and may otherwise be described as a "liquid bandage" in accordance with the Code of Federal Regulations (21CFR880.5090), that is a device that is used to cover an opening in the skin or as a dressing for burns or as a topical skin protectant. It is preferred that the aqueous wound healing formulation is for use primarily, or only, as a skin protectant and thus is a class I device in accordance with the above-mentioned Regulation.

Minor Injury to the Skin

In the present context, the term "minor injury to the skin" refers to small lesions to the skin or skin conditions that cause discomfort. The term is to be distinguished from injuries that require surgery or other conditions caused by more severe trauma to the body. Examples of minor injuries to the skin as referred to herein include, but are not limited to, cuts, abrasions, burns, blisters and calluses of the skin.

Such a minor injury to the skin is also referred to as a "wound" herein, although the minor injuries to the skin include also less acute conditions such as blisters and calluses. Thus, the terms "minor injury to the skin" and "wound" are used interchangeably herein.

Water-Soluble or Water-Dispersible

In the present context, the terms "water soluble" and "water-dispersible" refers to an entity, such as a polymeric material, that forms a solution or a dispersion, respectively, when added to an aqueous solvent. Solutions are homogenous mixtures of two or more substances that are composed of only a single phase. Dispersions are systems in which particles or droplets of one material are statistically distributed in a continuous phase of another material.

In the present context, the term "aqueous solvent" refers to a solvent with a content of water of at least 50 wt %, such as at least 60 wt %, such as at least 70 wt %, such as at least 80 wt %, such as at least 90 wt %, such as at least 95 wt %. The aqueous solvent may be water per se.

Adhering to the Skin

In the present context, the term "adhering to the skin" refers to the ability of a polymeric material to stick to the skin after the solvent of the polymeric material evaporates. The ability of adherence is therefore related to the polymeric material in substantially solvent-free and dry form and not as a liquid.

Film

In the present context, the term "film" refers to the thin layer or sheet comprising polymeric material left behind on the skin after the solvent of the aqueous formulation evaporates. The film is also referred to as a "protective film" and is applied to the skin to cover a desired affected area of the skin. The film is breathable and may take any shape and size depending on the amount and form of aqueous formulation applied.

Acrylate Copolymer

In the present context, the term "acrylate copolymer" refers to a copolymer comprising at least acrylate monomers. Copolymers are polymers derived from more than a single species of monomer, and include bipolymers, terpolymers and quaterpolymers, build from two, three and four different monomers, respectively. Acrylate copolymers as referred to herein may have monomers arranged in different structures, such as linear or branched, and block copolymers. Thus, acrylate copolymers may have different arrangements, but all comprise at least two different monomers, one of which is an acrylate monomer.

Thickening Agent

In the present context, the term "thickening agent" refers to substances that are capable of increasing the viscosity of liquids. Thickening agents can be added to a formulation without substantially altering any other property than the viscosity of the formulation.

Thickening agents may also be referred to as rheology modifiers.

Preservative Agent

In the present context, the term "preservative agent" refers to a substance that prevent fouling of a product due to harmful microbial growth or any other unwanted change of properties of the formulation. Preservative agent may be either a naturally occurring substance or a synthetically prepared chemical.

Thus, addition of a preservative agent reduces the risk of spoilage of a formulation.

Colouring Agent

In the present context, the term "colouring agent" refers to a coloured substance that when added to an aqueous formulation provides the formulation with colour. Colouring agents include, but are not limited to, dyes, pigments and lakes, and may be of natural or synthetic origin. Colouring agents may include dyes, pigments and/or lakes that in themselves soluble in water but also water insoluble dyes, pigments and/or lakes that through formulation as a colouring agent are made water-soluble.

Antiseptic Agent

In the present context, the term "antiseptic agent" refers to an antimicrobial substance that reduces the risk of infection when applied to a site of injury to the skin. Antiseptic agents may be bacteriocidal (i.e. capable of killing microbes) or bacteriostatic (i.e. preventing or inhibiting microbial growth).

Local Anaesthetic Agent

In the present context, the term "local anaesthetic agent" refers to a substance that eliminate or reduces the pain sensation in a specific and delimited area of the body. Local anaesthetic agent does not cause loss of consciousness as is the case with general anaesthetic agents.

As used herein, local anaesthetic agents refer to topical anaesthetic agents that assert their effect to the surface of a body part. They may be used to relieve pain and itching caused by e.g. cuts, scratches, abrasions, burns, sunburns, blisters, calluses, insect bites or stings.

Anti-Inflammatory Agent

In the present context, the term "anti-inflammatory agent" refers to a substance that reduces inflammation. Thus, application of an anti-inflammatory agent to a site of injury on the skin can reduce pain, swelling and redness. Anti-inflammatory agents include, but are not limited to, hormones, non-steroidal anti-inflammatory drugs (NSAIDs), and naturally occurring bioactive compounds that exhibit anti-inflammatory properties. The latter include eugenol, eucalyptol, menthone and menthol.

Botanical Ingredient

In the present context, the term "botanical ingredient" refers to a substance that originates from plants, such as herbs, roots, flowers, fruits, leaves, and seeds. Botanical ingredients may serve a variety of functions which include, but are not limited to, providing a soothing and comforting sensation, providing pleasant scents and aroma, nourishing and tightening of the skin, and being a source of antioxidants, vitamins and minerals.

Weight Percentage (wt %)

In the present context, the term "weight percentage" or "wt %" refers to the relative weight of the respective ingredient (polymer, thickening agent, preservative agent, antiseptic agent etc.) with respect to the total weight of the aqueous formulation, unless otherwise defined.

About

Wherever the term "about" is employed herein in the context of amounts, for example absolute amounts, such as numbers, purities, weights, sizes, etc., or relative amounts (e.g. percentages, equivalents or ratios), timeframes, and parameters such as temperatures, pressure, etc., it will be appreciated that such variables are approximate and as such may vary by ±10%, for example ±5% and preferably ±2% (e.g. ±1%) from the actual numbers specified. This is the case even if such numbers are presented as percentages in the first place (for example 'about 10%' may mean±10% about the number 10, which is anything between 9% and 11%).

Aqueous Wound Healing Formulation and Use as a Treatment for Minor Injuries to the Skin Minor injuries to the skin can be treated by application of a wound cover to the site of injury. Conventional bandages can let in water, dirt and unwanted microorganisms or simply unintentionally fall off leaving the injury vulnerable to infections. Additionally, use of the bandages can be uncomfortable with difficulties related to making the bandages stick or pain associated with removal of bandage. Liquid film-forming composition are advantageous for treatment of injuries such as cuts, abrasions, burns, blisters and calluses of the skin. Amongst the favourable attributes of dried films applied to the skin are high elasticity and comfort, water resistance and breathability.

Herein are provided wound healing formulations that are water-based and therefore highly compatible with application to the human or animal skin. The aqueous wound healing formulations can easily be applied and removed by any individual and untrained person without the assistance of medical personnel. The wound cover is made in situ by applying a sufficient amount of the aqueous wound healing formulation upon the site of injury on the skin, which then dries quickly by solvent evaporation to form a thin protective film. The quick drying period ensures that the aqueous wound healing formulation is simple and fast to use, which is particularly useful when treating impatient subjects, such as children or animals. The protective film covering the lesion of the skin can thereafter be easily and painlessly removed at the end of, or during, the healing process by simple washing with soap and water accompanied by scrubbing or alternatively by use of solvents, such as acetone. Importantly, the aqueous wound healing formulation provides a safe cover and protection of the affected area and enables healing of lesions in less accessible areas without any undue pain or irritation of the affected area.

Thus, an aspect of the present invention relates to a method of treatment of a minor injury to the skin, which method comprises topically applying to said injured area an aqueous formulation comprising a water-soluble or a water-dispersible polymeric material, which polymeric material is capable of:
(i) adhering to the skin; and
(ii) acting as a barrier to moisture but not to oxygen,
to cover said injured area, and then allowing water within the aqueous formulation to evaporate to leave a film comprising said polymeric material that covers said injured area, to treat said minor injury.

Given the water-based nature of the formulation the treatment is highly compatible with human and animal skin which is critical for a pleasant experience that avoids uncomfortable stinging or irritation of the skin. During treatment the protective film left behind as water evaporates from the formulation provides an effective shielding of the injury from the environment to exclude microorganisms and minimise risk of infection at the site of injury. While acting as an effective cover, the film has high breathability which ensures that the healing process can progress naturally. Consequently, there is no immediate need for exchanging the protective film frequently to keep the site of injury clean or provide oxygen to the wound.

Easy and fast transference of the protective film to the skin is important for a user-friendly experience. Conveniently, the film is attached to the skin by simply applying the aqueous formulation to the skin and allowing the aqueous solvent to evaporate. Depending on the thickness of the film applied, the drying time of the aqueous formulation may vary. The drying time may be defined as time required for formation of the film, i.e. without the film coming off upon movement of the site of injury. Thus, an embodiment of the present invention relates to the method of treatment as described herein, wherein the solvent within the aqueous formulation is allowed to evaporate for a period of time in the range of about 1 to about 10 minutes, such as between about 2 and about 6 minutes. Another embodiment of the present invention relates to the method of treatment as described herein, wherein the solvent within the aqueous formulation is allowed to evaporate for less than about 30 minutes, such as less than about 20 minutes, such as less than about 15 minutes, such as less than about 10 minutes, such as less than about 5 minutes.

The method of treatment is simple but may include provision of instructions to the end user on how to use the aqueous formulation and what properties to expect from the protective film once attached.

Thus, an embodiment of the present invention relates to the method of treatment as described herein, which method comprises providing said aqueous formulation along with instructions to an end user to carry out the method as described herein.

Another embodiment of the present invention relates to the method of treatment as described herein, wherein, when said water within the aqueous formulation evaporates to leave said film comprising said polymeric material, said film:
(i) covers and adheres to said injured area;
(ii) acts as a barrier to moisture; and
(iii) does not act as a barrier to oxygen.

As described herein, the wound coverings described herein, once formed upon the surface of the skin as films cover the wound by exhibiting a high degree of water resistance, to the extent that they are essentially waterproof.

In this respect, by 'water resistant' we include that, following evaporation of the aqueous solvent, the wound coverings (or films) are essentially impermeable to water. By 'essentially' impermeable, we include that the wound coverings (or films) are at least about 50% impermeable, including at least about 60% impermeable, especially at least about 70%, such as at least about 80%, impermeable to ingress of water through the polymer film as measured by CSN EN 13726-3, Test Methods for Primary Wound Dressings—Part 3: Waterproofness.

Thus, an embodiment of the present invention relates to the method of treatment as described herein, wherein said film is at least about 50% impermeable, such as at least about 60% impermeable to ingress of water through the polymer film.

Another embodiment of the present invention relates to the method of treatment as described herein, wherein the impermeable to ingress of water through the polymer film is measured in accordance with CSN EN 13726-3, Test Methods for Primary Wound Dressings—Part 3: Waterproofness.

On the other hand, as described herein, once formed on the surface of the skin, the wound coverings (or films) of the invention are permeable to gases, such as air/oxygen.

By 'permeable to air/oxygen' we include that, following evaporation of the aqueous solvent, the wound coverings (or films) are at least about 10% permeable, including at least about 15% impermeable, especially at least about 20%, such as at least about 25%, permeable, to air/oxygen.

Therefore, an embodiment of the present invention relates to the method of treatment as described herein, wherein said film is at least about 10% permeable, such as at least about 15% permeable, such as at least about 20% permeable, such as at least about 25% permeable to air/oxygen.

Another embodiment of the present invention relates to the method of treatment as described herein, wherein said film is at least about 50% impermeable, such as at least about 60% impermeable to ingress of water through the polymer film, and at least about 10% permeable, such as at least about 15% permeable, such as at least about 20% permeable, such as at least about 25% permeable to air/oxygen.

While it is important to avoid ingress of water and/or any contaminants from entering the area of the minor injury, it is also important to establish an environment at the site of the minor injury that supports the healing process. The moisture level is one factor that can be controlled to facilitate an efficient healing process. Specifically, the healing process is particularly hindered if the site of injury dries out. The moisture level may be assessed by the moisture vapour transmission rate (MVTR) as described in CSN EN 13726-2, Test Methods for Primary Wound Dressings—Part 2: Moisture vapour transmission rate of permeable film dressings. In this method the escape of vapor through the protective film is assessed.

Accordingly, an embodiment of the present invention relates to the method of treatment as described herein, wherein the moisture vapour transmission rate (MVTR) of said film is less than about 3000 g/m$^2$/24 hours, such as less than about 2800 g/m$^2$/24 hours, such as less than 2600 g/m$^2$/24 hours.

Another embodiment of the present invention relates to the method of treatment as described herein, wherein the moisture vapour transmission rate (MVTR) of said film is in the range of about 1000-4000 g/m$^2$/24 hours, such as 1500-3000 g/m$^2$/24 hours, such as 2000-2600 g/m$^2$/24 hours.

A further embodiment of the present invention relates to the method of treatment as described herein, wherein the moisture vapour transmission rate (MVTR) of said film is measured in accordance with CSN EN 13726-2, Test Methods for Primary Wound Dressings—Part 2: Moisture vapour transmission rate of permeable film dressings.

The protective film may easily and painlessly be removed from the skin by washing the film with water. It is to be understood that removal of the film may include using e.g. lukewarm or hot water and/or rubbing as required. Accordingly, the present method of treatment completely obviates the common occurrence of used bandages ripping of scab upon removal of the bandage, which is not only painful but also sets back the healing process.

Thus, an embodiment of the present invention relates to the method of treatment as described herein, wherein the method and/or instructions comprises the additional step of removing the film comprising the polymeric material by washing with water, as required.

While exchange of the protective film is not necessary per se it may be preferable in cases where the film has been damaged due to wear and tear or is excessively dirty.

Thus, an embodiment of the present invention relates to the method of treatment as described herein, wherein the method and/or instructions comprises the additional step of repeating the method as described herein, as required.

The method of treatment may be used to ameliorate or cure a variety of different injuries to the skin. The injuries are in many instances acute, such as cuts, burns and abrasions but may also have a more long-lasting or more permanent nature, such as blisters, calluses and ulcers. The present method of treatment is also useful against stinging sensations, e.g. in the event of insect bites and stings, in which case inclusion of local anaesthetic agents and/or antihistamines in the aqueous formulation may be beneficial.

Therefore, an embodiment of the present invention relates to the method of treatment as described herein, wherein the minor injury to the skin is selected from the group consisting of wounds, cuts, abrasions, burns, blisters, calluses, insect bites and stings.

Butterfly bandages and wound closure strips can be used to close small wounds. They are applied across a laceration in a manner which pulls the skin on either side of the wound together. The protective film described herein may equally well be used for these more demanding injuries. The protective film can be applied without need of professional medical assistance and will in many instances result in improved cosmetic outcomes as less scaring is expected than when using staples or sutures. It may also be preferred to use a liquid formulation for these types of minor open wounds since they are easy to use in highly contoured areas or parts of the body of musculoskeletal movements (e.g. joints) which are often prone to these types of injuries. Moreover, less pain is expected when applying a liquid formulation to areas of swelling, edema, hematoma or bloating as compared to conventional bandages, such as butterfly bandages or wound closure strips.

Thus, an embodiment of the present invention relates to the method of treatment as described herein, wherein the minor injury to the skin is a minor open wound.

The minor open wound does not necessarily have to be caused by an acute injury. Instead, a minor open wound may be caused by a planned procedure, such a surgery to the human or animal body. For planned procedures, the present method of treatment is favourable because the protective film can easily be applied to all areas of the body and efficiently protects the wound from infections.

Therefore, another embodiment of the present invention relates to the method of treatment as described herein, wherein the minor injury to the skin is a surgical wound, such as a minor surgical wound.

The aqueous formulation may be provided as an aqueous solution of the polymeric material that eventually forms the protective film. Such aqueous formulations are substantially free of organic solvents, such as alcohols, meaning that only minor amounts of organic solvents are present in the formulations.

Thus, an embodiment of the present invention relates to the method of treatment as described herein, wherein said aqueous formulation is an aqueous solution of said polymeric material.

It has been found advantageous to utilize a polymeric material comprising at least two different polymers to arrive at protective films with excellent performance, such as great water resistance, breathability, strength, flexibility, and ease of use.

Therefore, an embodiment of the present invention relates to the method of treatment as described herein, wherein the polymeric material comprises a combination of at least a first and a second polymer.

Vinyl polymers are a delimited group of polymers derived from vinyl monomers of the chemical formula $CH_2=CHR$. Their backbone is an extended alkane chain of the chemical formula $—CH_2—CHR—CH_2—CHR—$. The R group defines the specific type of vinyl polymers, such as R being $O_2CCH_3$ corresponding to polyvinyl acetate (PVAc). As noted from the chemical formula, PVAc belongs to the group of polyvinyl esters that are characterized by an R group being attached to the vinyl backbone by an ester bond, i.e with the general chemical formula $—RCO_2CHCH_2—$.

Thus, an embodiment of the present invention relates to the method of treatment as described herein, wherein the first polymer comprises a vinyl polymer.

Another embodiment of the present invention relates to the method of treatment as described herein, wherein the vinyl polymer is selected from the group consisting of polyvinyl acetate (PVAc), polyethylene, polypropylene, polystyrene, and polyacrylonitrile.

A further embodiment of the present invention relates to the method of treatment as described herein, wherein said vinyl polymer comprises a polyvinyl ester polymer.

Polyvinyl acetate (PVAc) is a polyvinyl ester may be prepared by conventional free-radical polymerization which makes it an atactic and highly branched polymer with no regular stereochemical configuration. Homopolymers of PVAc has a glass transition temperature around room temperature below which the polymer is quite brittle. Above the glass transition temperature, the polymer is very sticky, and exhibit resistance to UV and oxidation. PVAc is therefore known as an adhesive but is generally regarded as inappropriate for exterior use due to high water sensitivity of the homopolymer.

Polyvinyl ester polymers different from exist and may be formed either by direct polymerization or by ester exchange between PVAc and other esters or acids. Examples include, but are not limited to, polyvinyl butyrate, polyvinyl propionate, and polyvinyl formate.

Thus, an embodiment of the present invention relates to the method of treatment as described herein, wherein said polyvinyl ester polymer is selected from the group consisting of polyvinyl acetate (PvAc), polyvinyl benzoate, polyvinyl butyrate, polyvinyl formate, polyvinyl propionate, and polyvinyl stearate.

An assortment of chemically modified variants of PVAc also exist, with the most common one being polyvinyl alcohol (PVA). PVA may be prepared by hydrolyzing PVAc and yields a polymer with high tensile strength that depends in some degree on the amount of water in contact with the polymer. For that same reason PVA is amongst others used in re-moistenable adhesives. Derivatization of PVAc with aldehydes yields polyvinyl acetals, such as polyvinyl formal (PVF) and polyvinyl butyral (PVB). These may be prepared by reaction with formaldehyde and butyraldehyde, respectively. Both PVF and PVB exhibit good adhesive properties.

Therefore, an embodiment of the present invention relates to the method of treatment as described herein, wherein the first polymer comprises polyvinyl acetate (PVAc) or a derivative thereof.

Another embodiment of the present invention relates to the method of treatment as described herein, wherein the polyvinyl acetate (PVAc) or a derivative thereof is selected from the group consisting of polyvinyl actetate (PVAc), polyvinyl alcohol (PVA), polyvinyl formal (PVF), and polyvinyl butyral (PVB), and combinations thereof.

Copolymers of PVAc may be copolymerized with other monomers, e.g. to reduce the stiffness of the homopolymer. An example of such a copolymer is based on the monomer combination of vinyl acetate with ethylene, which yield ethylene vinyl acetate (EVA). Polymers of EVA are soft, tough, inert and have good adhesive properties.

Therefore, an embodiment of the present invention relates to the method of treatment as described herein, wherein the first polymer comprises a copolymer of polyvinyl acetate (PVAc). In other words, a copolymer of PVAc comprises monomers of vinyl acetate.

Another embodiment of the present invention relates to the method of treatment as described herein, wherein the first polymer comprises a copolymer of vinyl acetate and ethylene.

The inventors have found that a polymeric material comprising PVAc is advantageous for formation of durable protective films with good properties, such as water resistance. Notably, PVAc can readily be included in water-soluble or a water-dispersible polymeric material without need of any organic solvents.

Accordingly, an embodiment of the present invention relates to the method of treatment as described herein, wherein the first polymer comprises polyvinyl acetate.

The adhesive properties of PVAc can be affected by its mixture with other polymers and ingredients, such as thickeners and preservatives.

Therefore, an embodiment of the present invention relates to the method of treatment as described herein, wherein the amount of the first polymer is in the range of about 5 wt % to about 20 wt %, such as about 8 wt % to about 18 wt %, such as about 12 wt % to about 17 wt %, with respect to the total weight of said aqueous formulation.

The polymeric material may comprise two polymers, the second of which is selected to complement and enhance the properties of the first polymer. The second polymer may belong to the group of traditionally employed in emulsion polymer chemistry. Examples hereof include cellulose emulsion polymers, such as hydroxypropylcellulose, ethylcellulose and nitrocellulose. The inventors have found that acrylic polymers supplement the first polymer, such as PVAc, to yield a water-soluble or water-dispersible polymeric material with beneficial properties, such as water resistance, durability and great comfort. Acrylic polymers, also known simply as acrylics or acrylates, are polymer obtained from derivatives of acrylic acids and methacrylic acids.

Therefore, an embodiment of the present invention relates to the method of treatment as described herein, wherein the second polymer comprises an acrylic polymer.

The second polymer may be a copolymer of an acrylic polymer, also known as an acrylate copolymer. These polymers are typically excellent film forming polymers that can enhance water resistance. Acrylate copolymers therefore are suitable for use as part of the polymeric material. Accordingly, demonstrated herein are the applicability of several polyacrylate copolymers to yield protective films with excellent performance.

Thus, an embodiment of the present invention relates to the method of treatment as described herein, wherein the acrylic polymer is an acrylate copolymer.

A broad variety of acrylate copolymers exist. Common for most acrylate copolymers is that they can be used in water resistant formulations. One example is the copolymer prepared from acrylate and styrene monomers. Styrene is generally known to evaporate easily, and without being bound by theory, it is contemplated that the inclusion of styrene in the polymeric material may reduce drying time of the aqueous formulation upon application to the skin.

Therefore, an embodiment of the present invention relates to the method of treatment as described herein, wherein said acrylate copolymer comprises styrene or a derivative thereof.

A range of hydrophobic styrene-based monomers (or derivatives) may be suitable for the second polymer of the polymeric material. Examples of suitable styrene-based monomers include, but are not limited to, α-methyl styrene and alkyl-substituted styrenes, such as vinyl toluene and 4-methyl styrene. For the purposes of the polymeric material described herein, the styrene/acrylate copolymer has shown promising results, with certain ratios of between the first and second polymer being especially favourable.

Thus, a preferred embodiment of the present invention relates to the method of treatment as described herein, wherein said acrylate copolymer is a styrene/acrylate copolymer.

Another preferred embodiment of the present invention relates to the method of treatment as described herein, wherein the weight ratio between the first polymer and second polymer is in the range of about 3.2:1 to about 1:1, such as about 3.2:1 to about 1.5:1.

Another example of acrylate copolymers are copolymers comprising allyl methacrylate (AMA). AMA is an ester of methacrylic acid that readily forms copolymers with a long range of substances including, but not limited to, acrylic acid, amides, esters, methacrylates, acrylonitrile, maleic acid esters, vinyl acetate, vinyl chloride, vinylidene chloride, styrene, butadiene, and unsaturated polyesters. The aminomethyl propanol (AMP) salts of monomers of acrylic acid or methacrylic acid are known as AMP-acrylates. The copolymer of AMA and AMP-acrylate may be termed AMP-acrylate/AMA copolymer or AMP-acrylate/allyl methacrylate copolymer. This copolymer yielded particular beneficial characteristics when used as the second polymer of the polymeric material. Specific ratios of first polymer to AMP-acrylate/allyl methacrylate copolymer gave protective films with excellent properties, such as high water resistance, durability and good aesthetics.

Therefore, an embodiment of the present invention relates to the method of treatment as described herein, wherein said acrylate copolymer is a copolymer of allyl methacrylate and one or more monomers consisting of acrylic acid and/or methacrylic acid.

Another embodiment of the present invention relates to the method of treatment as described herein, wherein said acrylate copolymer is a copolymer of allyl methacrylate and an aminomethyl propanol salt of a monomer consisting of acrylic acid and/or methacrylic acid (AMP-acrylate).

A further embodiment of the present invention relates to the method of treatment as described herein, wherein the weight ratio between the first polymer and second polymer is in the range of about 8:1 to about 1:1, such as about 6:1 to about 2:1, such as about 5:1 to about 3:1.

Yet another embodiment of the present invention relates to the method of treatment as described herein, wherein the acrylate copolymer is a styrene/acrylate copolymer or an AMP-acrylate/allyl methacrylate copolymer.

Cyanoacrylates are derived from ethyl cyanoacrylate and thereto related esters. Cyanoacrylates are known as strong adhesives and have been used previously as topical skin adhesives under names such as Dermabond, SurgiSeal, GluStitch, LiquiBand and others. Amongst others, methyl 2-cyanoacrylate (MCA), ethyl 2-cyanoacrylate (ECA), n-butyl cyanoacrylate (n-BCA), octyl cyanoacrylate, and 2-octyl cyanoacrylate have been used extensively due to their adhesive strength. However, cyanoacrylates have previously been scrutinized for their negative impact on health. Specifically, cyanoacrylate-based glues or liquid bandages and their fumes can potentially cause chemical burns when applied to the skin in too large quantities. Moreover, cyanoacrylates are also considered to be a skin irritant that upon application to the skin cause stinging and in some individuals may lead to development of allergic skin reactions. Consequently, any topical formulations should ideally be devoid of cyanoacrylates.

Thus, an embodiment of the present invention relates to the method of treatment as described herein, wherein said aqueous formulation does not comprise any cyanoacrylate polymers.

Another embodiment of the present invention relates to the method of treatment as described herein, wherein said aqueous formulation does not comprise any cyanoacrylate polymers selected from the group consisting of methyl 2-cyanoacrylate (MCA), ethyl 2-cyanoacrylate (ECA), n-butyl cyanoacrylate (n-BCA), octyl cyanoacrylate, and 2-octyl cyanoacrylate, and combinations thereof.

The aqueous formulation may comprise one or more thickening agents, also known as rheology modifiers, to control the viscosity of the formulation. Particularly, the viscosity of the aqueous formulation may be modified to provide a formulation that is easy to apply to the skin. Many different groupings of thickening agents are available, and the aqueous formulation is not limited to a specific type of thickening agent. While the thickening agents in general do not alter any other properties of the aqueous formulation than the viscosity, some thickening agents are capable to influence water retention or improve scrub resistance. Thus, the thickening agent(s) and the amount thereof may be selected from a range of available substances.

Thus, an embodiment of the present invention relates to the method of treatment as described herein, wherein said aqueous formulation further comprises one or more thickening agents.

Another embodiment of the present invention relates to the method of treatment as described herein, wherein said one or more thickening agents are selected from the group consisting of cellulosics, gums, saccharides, proteins, organosilicones, and fumed silica, and combinations thereof.

A further embodiment of the present invention relates to the method of treatment as described herein, wherein said thickening agent comprises one or more cellulosics selected from the group consisting of hydroxyethyl cellulose (HEC), methyl hydroxy ethyl cellulose (MHEC), hydroxy propyl methyl cellulose (HPMC), ethyl hydroxy ethyl cellulose (EHEC), and carboxymethyl cellulose (CMC), and combinations thereof.

A still further embodiment of the present invention relates to the method of treatment as described herein, wherein said thickening agent comprises one or more saccharides selected from the group consisting of carrageenan, pullulan, konjac, and alginate, and combinations thereof.

An even further embodiment of the present invention relates to the method of treatment as described herein, wherein said thickening agent comprises one or more proteins selected from the group consisting of casein, collagen, and albumin, and combinations thereof.

Yet another embodiment of the present invention relates to the method of treatment as described herein, wherein said thickening agent comprises one or more organosilicones selected from the group consisting of silicone resins, dimethicones, and modified silicones, and combinations thereof.

The inventors have found that the use of gums, such as xanthan gum, as thickening agent yields aqueous formulations with viscosities appropriate for conveniently applying the formulation to the skin.

Accordingly, an embodiment of the present invention relates to the method of treatment as described herein, wherein said one or more thickening agents comprises a gum.

Another embodiment of the present invention relates to the method of treatment as described herein, wherein said gum is selected from the group consisting of xanthan, guar, cellulose, locust bean, and acacia, and combinations thereof.

A further embodiment of the present invention relates to the method of treatment as described herein, wherein said one or more thickening agents comprise or consist of xanthan gum.

Yet another embodiment of the present invention relates to the method of treatment as described herein, wherein the total amount of said one or more thickening agents in said aqueous formulation is in the range of about 0.5 wt % to about 2 wt %, such as about 0.8 wt % to about 1.5 wt %, preferably about 1.0 wt % to about 1.2 wt %, with respect to the total weight of said aqueous formulation.

It is recommended to avoid any microorganisms in the aqueous formulation both due to health concerns and because they can adversely affect the properties of the formulation, such as changes to viscosity, colour, pH or production of unpleasant odour. Most microorganisms thrive where water and nutrients are available to sustain their proliferation. Due to these moderate requirements, microorganisms can potentially proliferate in the aqueous formulation when stored or even after application to the skin.

To mitigate the risk of spoilage of the aqueous formulation one or more preservative agents may be included in the aqueous formulation. The preservative agent can be either a synthetic substance or a naturally occurring substance which prevent fouling of the aqueous formulation.

Therefore, an embodiment of the present invention relates to the method of treatment as described herein, wherein said aqueous formulation further comprises one or more preservative agents.

Another embodiment of the present invention relates to the method of treatment as described herein, wherein said one or more preservative agents are selected from the group consisting of phenoxyethanol, glycerin, methyl-4-hydroxy benzoate, propyl 4-hydroxybenzoate, butyl 4-hydroxybenzoate, triethylene glycol, benzyl alcohol, methylisothiazolinone, methylchloroisothiazolinone, diazolidinyl urea, imidazolidinyl urea, methylparaben, ethylparaben, propylparaben, butylparaben, and isobutylparaben, and combinations thereof.

A further embodiment of the present invention relates to the method of treatment as described herein, wherein said one or more preservative agents comprise or consist of phenoxyethanol and/or glycerin.

A still further embodiment of the present invention relates to the method of treatment as described herein, wherein the total amount of said one or more preservative agents in said aqueous formulation is in the range of about 0.5 wt % to about 2 wt %, such as about 0.7 wt % to about 1.5 wt %, preferably about 0.9 wt % to about 1.1 wt %, with respect to the total weight of said aqueous formulation.

One or more agents may be added to the aqueous formulation to soften the film and enhance its flexibility. One such agent is propylene glycol. Thus, an embodiment of the present invention relates to the method of treatment as described herein, wherein said aqueous formulation further comprises propylene glycol.

In contrast to conventional adhesive bandages or textile bandages, the aqueous formulation can be designed to be aesthetically pleasing to a broad selection of end users. The aqueous formulation may be transparent which gives a discrete look and provides the opportunity to largely conceal the protective film. A transparent protective film has the added benefit that it permits inspection of the healing process without the need to remove the protective film. Alternatively, the aqueous formulation may comprise one or more colouring agents to customize the look of the protective film. This option may especially appeal to children that can select their favourite colour and apply it to the skin with a brush as if they were painting.

Thus, an embodiment of the present invention relates to the method of treatment according to any one of the preceding claims, wherein said aqueous formulation and/or film is substantially transparent.

Another embodiment of the present invention relates to the method of treatment as described herein, wherein said aqueous formulation further comprises one or more colouring agents.

Colouring agents may include, but are not limited to, dyes and pigments. Dyes are defined as substances which upon dissolution dyes a solution through ionic or chemical interaction with a substrate. Pigments are insoluble fine powders that create colours via its own spectral absorption or reflection of specific wavelengths of lights.

Therefore, an embodiment of the present invention relates to the method of treatment as described herein, wherein said one or more colouring agents are dyes or pigments.

Another embodiment of the present invention relates to the method of treatment as described herein, wherein said one or more colouring agents are artificial colouring agents or natural colouring agents.

The colouring may be, but are in no way limited to the group: titanium dioxide coated mica and/or metal-based pigments, such as manganese violet coated with various silicone coatings and titanium dioxide pigment. In this manner the aqueous formulation can be provided in a colour favoured by the end user, such as a child. Colouring agents of many different colours may be utilised, the skilled person is capable of selecting colouring agents suitable for incorporation in an aqueous formulation as described herein. Mica and titanium dioxide may also be used to add a pearl effect or add aesthetic effects upon dry down of the film.

A further embodiment of the present invention relates to the method of treatment as described herein, wherein the total amount of said one or more colouring agents in said aqueous formulation is in the range of about 0.1 wt % to about 15 wt %, such as about 1 wt % to about 12 wt %, such as about 2 wt % to about 10 wt %, with respect to the total weight of said aqueous formulation.

The aqueous formulation may comprise one or more additives to prepare protective films suitable for different situations. If the method of treatment is used in a clinical setting it may for instance be particularly useful to add an antiseptic agent and/or anti-inflammatory agent to minimise risk of infection and reduce swelling and pain at the site of injury. Children may prefer an aqueous formulation comprising a local anaesthetic agent to ameliorate any immediate local pain after the injury occurred. Antihistamines can be included in aqueous formulations to reduce risk of allergic reactions, e.g. in the event of an insect bite. Some botanical ingredients are known to provide soothing and comforting sensations as well as providing pleasant scents. Consequently, a variety of combinations of additives may be contemplated depending on the type of minor injury to the skin and the purpose of the treatment. Thus, the present aqueous formulation is not limited to comprising any one specific additive or combinations thereof.

Accordingly, an embodiment of the present invention relates to the method of treatment as described herein, wherein said aqueous formulation further comprises one or more additives selected from the group consisting of antiseptic agents, local anaesthetic agents, anti-inflammatory agents, antihistamines, and botanical ingredients, and combinations thereof.

Antiseptic agents may be bacteriocidal (i.e. capable of killing microbes) or bacteriostatic (i.e. preventing or inhibiting microbial growth). Both types of antiseptic agents are suitable for the present aqueous formulation and a person skilled in art would be capable of selecting an appropriate antiseptic agent for topical use. One antiseptic agent with broad spectrum bacteriocidal activity is benzethonium chloride, also known as hyamine. This compound is a quaternary ammonium compound that is soluble in water and suitable for topical use. Relatively minute amounts of antiseptic agents are needed to provide the desired effect, and e.g. benzethonium chloride may be included in the aqueous formulation without affecting adversely any other properties of the formulation.

Thus, an embodiment of the present invention relates to the method of treatment as described herein, wherein said aqueous formulation further comprise one or more antiseptic agents.

Another embodiment of the present invention relates to the method of treatment as described herein, wherein said one or more antiseptic agents are selected from the group consisting of benzethonium chloride, chlorhexidine, chloroxylenol, isopropyl alcohol, hexachlorophene, benzalkonium chloride, and hydrogen peroxide, and combinations thereof.

A further embodiment of the present invention relates to the method of treatment as described herein, wherein said one or more antiseptic agents comprise or consist of benzethonium chloride.

Yet another embodiment of the present invention relates to the method of treatment as described herein, wherein the total amount of said one or more antiseptic agents in said aqueous formulation is in the range of about 0.1 wt % to about 0.5 wt %, preferably about 0.1 wt % to about 0.3 wt %, with respect to the total weight of said aqueous formulation.

Local anaesthetic agents can efficiently and fast relieve pain when applied to a specific position of the body. Thus, inclusion of local anaesthetic agents in the aqueous formulation may in particular be beneficial for treatment of injuries associated with aggravated pain or for treatment of children that may be more susceptible to the pain sensation.

In the present context, the term "local anaesthetic agent" refers to a substance that eliminate or reduces the pain sensation in a specific and delimited area of the body. Local anaesthetic agent does not cause loss of consciousness as is the case with general anaesthetic agents.

Thus, an embodiment of the present invention relates to the method of treatment as described herein, wherein said aqueous formulation further comprises one or more local anaesthetic agents.

The present method of treatment relies on topical application of the aqueous formulation to form a protective film on the skin. Therefore, the local anaesthetic agent should also be capable of asserting its effect through the skin. A person skilled in the art is capable of selecting local anaesthetic agents with a mode of action suitable for topical use.

Thus, an embodiment of the present invention relates to the method of treatment as described herein, wherein said one or more local anaesthetic agents are topical anaesthetic agents.

Another embodiment of the present invention relates to the method of treatment as described herein, wherein said one or more local anaesthetic agents are selected from the group consisting of lidocaine, benzocaine, butamben, dibucaine, oxybuprocaine, pramoxine, proxymetacaine, and tetracaine, and combinations thereof.

A further embodiment of the present invention relates the method of treatment as described herein, wherein said one or more local anaesthetic agents comprise or consist of lidocaine and/or benzocaine.

A still further embodiment of the present invention relates the method of treatment as described herein, wherein the total amount of said one or more local anaesthetic agents in said aqueous formulation is in the range of about 0.1 wt % to about 20 wt %, with respect to the total weight of said aqueous formulation.

Anti-inflammatory agents ameliorate pain by reducing the amount of inflammation at the site of injury. This is in contrast to any medical agents that assert their pain-relieving effect by blocking pain signalling to the brain, such as opioids. Hormones, such as steroid hormones, have good anti-inflammatory properties and have previously been utilized in topical treatments. Likewise, there exist a wide variety of nonsteroidal anti-inflammatory drugs (NSAIDs) that can be distinguished from the steroid hormones by not having a steroid chemical structure. While most NSAIDS are for systemic use, there are also available NSAIDs for topical use. Naturally occurring bioactive compounds that exhibit anti-inflammatory properties may also be included in the aqueous formulation.

Thus, an embodiment of the present invention relates to the method of treatment as described herein, wherein said aqueous formulation further comprises one or more anti-inflammatory agents.

Another embodiment of the present invention relates to the method of treatment as described herein, wherein said anti-inflammatory agent is a bioactive agent selected from the group consisting of eugenol, eucalyptol, menthone, and menthol, and combinations thereof.

A further embodiment of the present invention relates to the method of treatment as described herein, wherein said one or more anti-inflammatory agents are hormones and/or nonsteroidal anti-inflammatory drugs (NSAIDs).

A group of steroid hormones that exhibit good anti-inflammatory effects when applied topically is glucocorticoids. In some situations, the addition of glucocorticoids in the aqueous formulation may be favourable, including, but not limited to, treatment of insect bites and stings.

Therefore, an embodiment of the present invention relates to the method of treatment as described herein, wherein said anti-inflammatory agent is a glucocorticoid.

Another embodiment of the present invention relates to the method of treatment as described herein, wherein said anti-inflammatory agent is a glucocorticoid selected from the group consisting of cortisone, alclometasone, dexamethasone, and triamcinolone, and combinations thereof.

A further embodiment of the present invention relates to the method of treatment as described herein, wherein said one or more anti-inflammatory agents comprise or consist of cortisone.

A still further embodiment of the present invention relates to the method of treatment as described herein, wherein the total amount of said one or more anti-inflammatory agents in said aqueous formulation is in the range of about 0.1 wt % to about 10 wt %, with respect to the total weight of said aqueous formulation.

Botanical ingredients may be included in the aqueous formulation to increase comfort of the protective film by providing a pleasant scent or a soothing sensation. However, botanical ingredients may also have documented medical effects that facilitate the healing process of the injury to the skin.

Thus, an embodiment of the present invention relates to the method of treatment as described herein, wherein said aqueous formulation further comprises one or more botanical ingredients.

An embodiment of the present invention relates to the method of treatment as described herein, wherein said one or more botanical ingredients are selected from the group consisting of herbs, roots, flowers, fruits, leaves, and seeds, and combinations thereof.

A further embodiment of the present invention relates to the method of treatment as described herein, wherein said one or more botanical ingredients are selected from the group consisting of aloe, chamomile, lavender, tea tree oil, calendula, dandelion, and lotus, and combinations thereof.

Another embodiment of the present invention relates to the method of treatment as described herein, wherein the total amount of said one or more botanical ingredients in said aqueous formulation is in the range of about 0.1 wt % to about 25 wt %, such as about 1 wt % to about 20 wt %, about 2 wt % to about 15 wt %, with respect to the total weight of said aqueous formulation.

Yet another embodiment of the present invention relates to the method of treatment as described herein, wherein said one or more botanical ingredients are selected from the group consisting of aloe, chamomile, and lavender and combinations thereof.

The method of treatment is based on the topical application of an aqueous formulation comprising a water-soluble or water-dispersible polymeric material to a minor injury to the skin. The water-based formulation ensures exceptional compatibility with skin and obviates the nuisances that are typically associated with formulation based on organic solvents, such as stinging.

Thus, an embodiment of the present invention relates to the method of treatment as described herein, wherein said aqueous formulation is substantially free of organic solvents.

Another embodiment of the present invention relates to the method of treatment as described herein, wherein said aqueous formulation is substantially free of alcohol.

As used herein, substantially free of organic solvents or alcohol means that the aqueous formulation comprises less than 10 wt % organic solvent or alcohol, such as less than 5 wt %, such as less than 4 wt %, such as less than 3 wt %, such as less than 2 wt % organic solvent or alcohol.

The aqueous formulation as described herein may also be used for preventive and/or inhibitory purposes, e.g. in situations wherein the skin is expected to be subject to friction, chaffing, bruising or cuts. Preventive and inhibitory means may especially be necessary in areas where the skin is expected to be exposed to many irritants. One example may be the area in which a diaper is applied, since this area is subject to excessive friction and irritants, such as urine and faeces. Therefore, the aqueous formulation may be applied to the skin as a preventive means for avoiding e.g. cuts, blisters, rashes or similar minor injuries.

Accordingly, an embodiment of the present invention relates to the method of treatment, wherein the aqueous formulation is applied to the skin as a preventive or inhibitory treatment.

The method of treatment is easy to perform for any individual and present an improved protective film with excellent performance of the aqueous formulation without any irritation of the skin.

Thus, an aspect of the present invention relates to an aqueous wound healing formulation comprising:
(i) a water-soluble or a water-dispersible polymeric material comprising:
  a first polymer comprising a vinyl polymer, and
  a second polymer comprising an acrylic polymer;
(ii) optionally, one or more thickening agents; and
(iii) optionally, one or more preservative agents.

The aqueous wound formulation is suitable for use in a method of treatment as described herein. It is therefore to be understood that the embodiments of the present invention described herein in relation to the method of treatment are equally compatible with the aqueous wound healing formulation per se.

The meaning of "wound" is as defined herein, i.e. it is used to describe the minor injury to the skin that the aqueous wound healing formulation is suitable for treating, such as, but not limited to, wounds, cuts, abrasions, burns, blisters, calluses, insect bites and stings.

Aqueous wound healing formulations with certain combinations of components have shown to yield especially favourable protective films when applied to the skin.

Thus, an embodiment of the present invention relates to the aqueous wound healing formulation as described herein, wherein said aqueous wound healing formulation comprises:
(i) a water-soluble or a water-dispersible polymeric material comprising:
  polyvinyl acetate, and
  AMP-acrylate/allyl methacrylate copolymer or styrene/acrylate copolymer;
(ii) one or more thickening agents; and
(iii) one or more preservative agents.

Another embodiment of the present invention relates to the aqueous wound healing formulation as described herein, wherein said aqueous wound healing formulation comprises:
(i) a water-soluble or a water-dispersible polymeric material comprising:
  polyvinyl acetate, and
  AMP-acrylate/allyl methacrylate copolymer or styrene/acrylate copolymer;
(ii) one or more thickening agents;
(iii) one or more preservative agents; and
(iv) one or more colouring agents.

A further embodiment of the present invention relates to the aqueous wound healing formulation as described herein, wherein said aqueous wound healing formulation comprises:
(i) a water-soluble or a water-dispersible polymeric material comprising:
  polyvinyl acetate, and
  AMP-acrylate/allyl methacrylate copolymer or styrene/acrylate copolymer;
(ii) one or more thickening agents;
(iii) one or more preservative agents;
(iv) optionally, one or more colouring agents; and
(v) one or more additives selected from the group consisting of antiseptic agents, local anaesthetic agents, anti-inflammatory agents, antihistamines, and botanical ingredients, and combinations thereof.

A still further embodiment of the present invention relates to the aqueous wound healing formulation as described herein, wherein said aqueous wound healing formulation comprises:
(i) a water-soluble or a water-dispersible polymeric material comprising:
  polyvinyl acetate, and
  AMP-acrylate/allyl methacrylate copolymer or styrene/acrylate copolymer;
(ii) xanthan gum;
(iii) phenoxyethanol and/or glycerin;
(iv) optionally, one or more colouring agents;
(v) benzethonium chloride and/or lidocaine and/or benzocaine.

An even further embodiment of the present invention relates to the aqueous wound healing formulation as described herein, wherein said aqueous wound healing formulation comprises:
(i) a water-soluble or a water-dispersible polymeric material comprising:
  polyvinyl acetate, and
  AMP-acrylate/allyl methacrylate copolymer or styrene/acrylate copolymer;
(ii) xanthan gum;
(iii) phenoxyethanol and/or glycerin;
(iv) optionally, one or more colouring agents; and
(v) cortisone.

Yet another embodiment of the present invention relates to the aqueous wound healing formulation as described herein, wherein said aqueous wound healing formulation comprises:
(i) a water-soluble or a water-dispersible polymeric material comprising:
  polyvinyl acetate, and
  AMP-acrylate/allyl methacrylate copolymer or styrene/acrylate copolymer;
(ii) xanthan gum;
(iii) phenoxyethanol and/or glycerin; and
(iv) one or more botanical ingredients.

These favourable formulations may clearly be used in the method of treatment described herein.

The aqueous wound healing formulation may be packaged in a container for storage until use. By storing the formulation in a container, such as a bottle, the amount of environmentally polluting packaging material can be reduced dramatically. For example, a bottle containing 0.3 oz is estimated to account for 100 uses, meaning 100 less wrappings to decompose for each bottle sold. In addition, the use of a liquid formulation itself also saves the trashing of a plastic and/or textile bandage for each use. Consequently, there is an environmental benefit associated with the aqueous wound healing formulation provided herein.

Thus, an aspect of the present invention relates to a container comprising an aqueous wound healing formulation as described herein.

The container can be adapted to suit the specific manner for applying the aqueous wound healing formulation to the skin, including, but not limited to, brush-on and spraying. Brush-on applicators (or pens) are a popular choice for applying liquid bandages as the method is gently yet easy and precise to perform. Spraying has the advantage that there is no need to touch the site of injury and therefore aqueous formulations may be applied with a minimum of discomfort. If intended for spraying, the aqueous wound healing formulation may be packed in a propellant gas spray pack.

Therefore, an embodiment of the present invention relates to the as described herein, wherein the container is of a type selected from the group consisting of bottles, spray packs, daubers and droppers.

Another embodiment of the present invention relates to the container as described herein, wherein the container comprises a means for applying the aqueous wound healing formulation to the skin.

A preferred embodiment of the present invention relates to the container as described herein, wherein the container is a bottle.

A further embodiment of the present invention relates to the container as described herein, wherein the bottle comprises a lid comprising an applicator brush.

The aqueous wound healing formulation may be prepared a simple mixing procedure wherein the first and second polymers of the polymeric material is added sequentially into the aqueous solvent under agitation. Any thickening agents are added before the polymeric material, whereas any preservative agent is added after the polymeric material.

Thus, an aspect of the present invention relates to use of a water-soluble or a water-dispersible polymeric material comprising a first polymer which is a vinyl polymer, and a second polymer which is an acrylic polymer, for preparation of an aqueous wound healing formulation.

Another aspect of the present invention relates to a method for producing an aqueous wound healing formulation as described herein, said method comprising the steps of:
(i) providing a mixing container comprising an aqueous solvent,
(ii) adding the first polymer to said mixing container under stirring, and
(iii) adding the second polymer to said mixing container under stirring.

It is to be understood that the embodiments of the present invention described herein in relation to the method of treatment and/or aqueous wound healing formulation are equally compatible with these two aspects of the invention. Specifically, the definition of the first and second polymers may be applied also to these two aspects.

An embodiment of the present invention relates to the method as described herein, further comprising a step of adding a thickening agent to the aqueous solvent before adding said first polymer.

Another embodiment of the present invention relates to the method as described herein, further comprising a step of adding a preservative to the mixing container after adding said second polymer.

The aqueous wound healing formulation is suitable for use in the treatment of minor injuries to the skin and in some forms also as a medicament for efficiently progressing the healing process.

Therefore, an aspect of the present invention relates to an aqueous wound healing formulation as described herein for use as a medicament.

Another aspect of the present invention relates to an aqueous wound healing formulation as described herein for use in the treatment of a minor injury to the skin.

An embodiment of the present invention relates to the aqueous wound healing formulation for use as described herein, wherein the minor injury to the skin is selected from the group consisting of wounds, cuts, abrasions, burns, blisters, calluses, insect bites and stings.

Another embodiment of the present invention relates to the aqueous wound healing formulation for use as described herein, wherein said aqueous wound healing formulation is applied topically to the skin.

The aqueous wound healing formulation may conveniently be provided as part of a kit with instructions on e.g. how and when to use the formulation.

Therefore, an aspect of the present invention relates to a kit-of-parts comprising:
(i) an aqueous wound healing formulation as described herein and optionally a means for applying the aqueous wound healing formulation to the skin; or
(ii) a container as described herein; and
(iii) instructions for use.

The listing or discussion of an apparently prior published document in this specification should not necessarily be taken as an acknowledgement that the document is part of the state of the art or is common general knowledge.

Preferences, options and embodiments for a given aspect, feature or parameter of the invention should, unless the context indicates otherwise, be regarded as having been disclosed in combination with any and all preferences, options and embodiments for all other aspects, features and parameters of the invention. This is especially true for the description of the method of treatment and all its features, which may readily be projected to the aqueous wound healing formulation and use of the same as described herein.

Clauses

Embodiments and features of the present invention are also illustrated in the following clauses.

1. A method of treatment of a minor injury to the skin, which method comprises topically applying to said injured area an aqueous formulation comprising a water-soluble or a water-dispersible polymeric material, which polymeric material is capable of:
(i) adhering to the skin; and
(ii) acting as a barrier to moisture but not to oxygen,
to cover said injured area, and then allowing water within the aqueous formulation to evaporate to leave a film comprising said polymeric material that covers said injured area, to treat said minor injury.

2. The method of treatment according to clause 1, which method comprises providing said aqueous formulation along with instructions to an end user to carry out the method according to clause 1.

3. The method of treatment according to any one of clauses 1 or 2, wherein, when said water within the aqueous formulation evaporates to leave said film comprising said polymeric material, said film:
(i) covers and adheres to said injured area;
(ii) acts as a barrier to moisture; and
(iii) does not act as a barrier to oxygen.

4. The method of treatment according to any one of the preceding clauses, wherein the method and/or instructions comprises the additional step of removing the film comprising the polymeric material by washing with water, as required.

5. The method of treatment according to clause 4, wherein the method and/or instructions comprises the additional step of repeating the method defined in clause 1, as required.

6. The method of treatment according to any one of the preceding clauses, wherein the minor injury to the skin is selected from the group consisting of wounds, cuts, abrasions, burns, blisters, calluses, insect bites and stings.

7. The method of treatment according to any one of the preceding clauses, wherein said aqueous formulation is an aqueous solution of said polymeric material.

8. The method of treatment according to any one of the preceding clauses, wherein the polymeric material comprises a combination of at least a first and a second polymer.

9. The method of treatment according to clause 8, wherein the first polymer comprises a vinyl polymer.

10. The method of treatment according to clause 9, wherein said vinyl polymer comprises a polyvinyl ester polymer.

11. The method of treatment according to clause 10, wherein said polyvinyl ester polymer is selected from the group consisting of polyvinyl acetate (PVAc), polyvinyl benzoate, polyvinyl butyrate, polyvinyl formate, polyvinyl propionate, and polyvinyl stearate.

12. The method of treatment according to any one of clauses 8-11, wherein the first polymer comprises polyvinyl acetate.

13. The method of treatment according to any one of clauses 8-12, wherein the amount of the first polymer is in the range of about 5 wt % to about 20 wt %, such as about 8 wt % to about 18 wt %, such as about 12 wt % to about 17 wt %, with respect to the total weight of said aqueous formulation.

14. The method of treatment according to any one of clauses 8-13, wherein the second polymer comprises an acrylic polymer.

15. The method of treatment according to clause 14, wherein the acrylic polymer is an acrylate copolymer.

16. The method of treatment according to clause 15, wherein said acrylate copolymer comprises styrene or a derivative thereof.

17. The method of treatment according to any one of clauses 15 or 16, wherein said acrylate copolymer is a styrene/acrylate copolymer.

18. The method of treatment according to any one of clauses 8-17, wherein the weight ratio between the first polymer and second polymer is in the range of about 3.2:1 to about 1:1, such as about 3.2:1 to about 1.5:1.

19. The method of treatment according to clause 15, wherein said acrylate copolymer is a copolymer of allyl methacrylate and one or more monomers consisting of acrylic acid and/or methacrylic acid.

20. The method of treatment according to clause 19, wherein said acrylate copolymer is a copolymer of allyl methacrylate and an aminomethyl propanol salt of a monomer consisting of acrylic acid and/or methacrylic acid (AMP-acrylate).

21. The method of treatment according to any one of clauses 19 or 20, wherein the weight ratio between the first polymer and second polymer is in the range of about 8:1 to about 1:1, such as about 6:1 to about 2:1, such as about 5:1 to about 3:1.

22. The method of treatment according to any one of the preceding clauses, wherein said aqueous formulation does not comprise any cyanoacrylate polymers.

23. The method of treatment according to any one of the preceding clauses, wherein said aqueous formulation further comprises one or more thickening agents.

24. The method of treatment according to clause 23, wherein said one or more thickening agents are selected from the group consisting of cellulosics, gums, saccharides, proteins, organosilicones, and fumed silica, and combinations thereof.

25. The method of treatment according to any one of clauses 23 or 24, wherein said one or more thickening agents comprises a gum.

26. The method of treatment according to any one of clauses 24 or 25, wherein said gum is selected from the group consisting of xanthan, guar, cellulose, locust bean, and acacia, and combinations thereof.

27. The method of treatment according to any one of clauses 23-26, wherein said one or more thickening agents comprise or consist of xanthan gum.

28. The method of treatment according to any one of clauses 23-27, wherein the total amount of said one or more thickening agents in said aqueous formulation is in the range of about 0.5 wt % to about 2 wt %, such as about 0.8 wt % to about 1.5 wt %, preferably about 1.0 wt % to about 1.2 wt %, with respect to the total weight of said aqueous formulation.

29. The method of treatment according to any one of the preceding clauses, wherein said aqueous formulation further comprises one or more preservative agents.

30. The method of treatment according to clause 29, wherein said one or more preservative agents are selected from the group consisting of phenoxyethanol, glycerin, methyl-4-hydroxy benzoate, propyl 4-hydroxybenzoate, butyl 4-hydroxybenzoate, triethylene glycol, benzyl alcohol, methylisothiazolinone, methylchloroisothiazolinone, diazolidinyl urea, imidazolidinyl urea, methylparaben, ethylparaben, propylparaben, butylparaben, and isobutylparaben, and combinations thereof.

31. The method of treatment according to any one of clauses 29 or 30, wherein said one or more preservative agents comprise or consist of phenoxyethanol and/or glycerin.

32. The method of treatment according to any one of clauses 29-31, wherein the total amount of said one or more preservative agents in said aqueous formulation is in the range of about 0.5 wt % to about 2 wt %, such as about 0.7 wt % to about 1.5 wt %, preferably about 0.9 wt % to about 1.1 wt %, with respect to the total weight of said aqueous formulation.

33. The method of treatment according to any one of the preceding clauses, wherein said aqueous formulation further comprises one or more colouring agents.

34. The method of treatment according to clause 33, wherein said one or more colouring agents are dyes or pigments.

35. The method of treatment according to any one of clauses 33 or 34, wherein said one or more colouring agents are artificial colouring agents or natural colouring agents.

36. The method of treatment according to any one of clauses 33-35, wherein the total amount of said one or more colouring agents in said aqueous formulation is in the range of about 0.1 wt % to about 15 wt %, such as about 1 wt % to about 12 wt %, such as about 2 wt % to about 10 wt %, with respect to the total weight of said aqueous formulation.

37. The method of treatment according to any one of the preceding clauses, wherein said aqueous formulation further comprises one or more additives selected from the group consisting of antiseptic agents, local anaesthetic agents, anti-inflammatory agents, antihistamines, and botanical ingredients, and combinations thereof.

38. The method of treatment according to any one of the preceding clauses, wherein said aqueous formulation further comprise one or more antiseptic agents.

39. The method of treatment according to any one of clauses 37 or 38, wherein said one or more antiseptic agents are selected from the group consisting of benzethonium chloride, chlorhexidine, chloroxylenol, isopropyl alcohol, hexachlorophene, benzalkonium chloride, and hydrogen peroxide, and combinations thereof.

40. The method of treatment according to any one of clauses 37-39, wherein said one or more antiseptic agents comprise or consist of benzethonium chloride.

41. The method of treatment according to any one of clauses 37-40, wherein the total amount of said one or more antiseptic agents in said aqueous formulation is in the range of about 0.1 wt % to about 0.5 wt %, preferably about 0.1 wt % to about 0.3 wt %, with respect to the total weight of said aqueous formulation.

42. The method of treatment according to any one of the preceding clauses, wherein said aqueous formulation further comprises one or more local anaesthetic agents.

43. The method of treatment according to clause 42, wherein said one or more local anaesthetic agents are selected from the group consisting of lidocaine, benzocaine, butamben, dibucaine, oxybuprocaine, pramoxine, proxymetacaine, and tetracaine, and combinations thereof.

44. The method of treatment according to any one of clauses 42 or 43, wherein said one or more local anaesthetic agents comprise or consist of lidocaine and/or benzocaine.

45. The method of treatment according to any one of clauses 42-44, wherein the total amount of said one or more local anaesthetic agents in said aqueous formulation is in the range of about 0.1 wt % to about 20 wt %, with respect to the total weight of said aqueous formulation.

46. The method of treatment according to any one of the preceding clauses, wherein said aqueous formulation further comprises one or more anti-inflammatory agents.

47. The method of treatment according to clause 46, wherein said one or more anti-inflammatory agents are hormones and/or nonsteroidal anti-inflammatory drugs (NSAIDs).

48. The method of treatment according to any one of clauses 46 or 47, wherein said one or more anti-inflammatory agents comprise or consist of cortisone.

49. The method of treatment according to any one of clauses 46-48, wherein the total amount of said one or more anti-inflammatory agents in said aqueous formulation is in the range of about 0.1 wt % to about 10 wt %, with respect to the total weight of said aqueous formulation.

50. The method of treatment according to any one of the preceding clauses, wherein said aqueous formulation further comprises one or more botanical ingredients.

51. The method of treatment according to clause 50, wherein said one or more botanical ingredients are selected from the group consisting of herbs, roots, flowers, fruits, leaves, and seeds, and combinations thereof.

52. The method of treatment according to any one of clauses 50 or 51, wherein said one or more botanical ingredients are selected from the group consisting of aloe, chamomile, lavender, tea tree oil, calendula, dandelion, and lotus, and combinations thereof.

53. The method of treatment according to any one of the preceding clauses, wherein said aqueous formulation is substantially free of organic solvents.

54. The method of treatment according to any one of the preceding clauses, wherein said aqueous formulation is substantially free of alcohol.

55. An aqueous wound healing formulation comprising:
 (i) a water-soluble or a water-dispersible polymeric material comprising:
  a first polymer comprising a vinyl polymer, and
  a second polymer comprising an acrylic polymer;
 (ii) optionally, one or more thickening agents; and
 (iii) optionally, one or more preservative agents.

56. The aqueous wound healing formulation according to clause 55, wherein said vinyl polymer comprises a polyvinyl ester polymer.

57. The aqueous wound healing formulation according to clause 56, wherein said polyvinyl ester polymer is selected from the group consisting of polyvinyl acetate (PVAc), polyvinyl benzoate, polyvinyl butyrate, polyvinyl formate, polyvinyl propionate, and polyvinyl stearate.

58. The aqueous wound healing formulation according to any one of clauses 55-57, wherein the first polymer comprises polyvinyl acetate.

59. The aqueous wound healing formulation according to any one of clauses 55-58, wherein the amount of the first polymer is in the range of about 5 wt % to about 20 wt %, such as about 8 wt % to about 18 wt %, such as about 12 wt % to about 17 wt %, with respect to the total weight of said aqueous wound healing formulation.

60. The aqueous wound healing formulation according to any one of clauses 55-59, wherein the acrylic polymer is an acrylate copolymer.

61. The aqueous wound healing formulation according to clause 60, wherein said acrylate copolymer comprises styrene or a derivative thereof.

62. The aqueous wound healing formulation according to any one of clauses 60 or 61, wherein said acrylate copolymer is a styrene/acrylate copolymer.

63. The aqueous wound healing formulation according to any one of clauses 60-62, wherein the weight ratio between the first polymer and second polymer is in the range of about 3.2:1 to about 1:1, such as about 3.2:1 to about 1.5:1.

64. The aqueous wound healing formulation according to clause 60, wherein said acrylate copolymer is a copolymer of allyl methacrylate and one or more monomers consisting of acrylic acid and/or methacrylic acid.

65. The aqueous wound healing formulation according to clause 64, wherein said acrylate copolymer is a copolymer of allyl methacrylate and an aminomethyl propanol salt of a monomer consisting of acrylic acid and/or methacrylic acid (AMP-acrylate).

66. The aqueous wound healing formulation according to any one of clauses 64 or 65, wherein the weight ratio between the first polymer and second polymer is in the range of about 8:1 to about 1:1, such as about 6:1 to about 2:1, such as about 5:1 to about 3:1.

67. The aqueous wound healing formulation according to any one of clauses 55-66, wherein said aqueous wound healing formulation does not comprise any cyanoacrylate polymers.

68. The aqueous wound healing formulation according to any one of clauses 55-67, wherein said aqueous wound healing formulation comprises one or more thickening agents.

69. The aqueous wound healing formulation according to any one of clauses 55-68, wherein said one or more thickening agents are selected from the group consisting of cellulosics, gums, saccharides, proteins, organosilicones, and fumed silica, and combinations thereof.

70. The aqueous wound healing formulation according to any one of clauses 55-69, wherein said one or more thickening agents comprises a gum.

71. The aqueous wound healing formulation according to any one of clauses 69 or 70, wherein said gum is selected from the group consisting of xanthan, guar, cellulose, locust bean, and acacia, and combinations thereof.

72. The aqueous wound healing formulation according to any one of clauses 55-71, wherein said one or more thickening agents comprise or consist of xanthan gum.

73. The aqueous wound healing formulation according to any one of clauses 55-72, wherein the total amount of said one or more thickening agents is in the range of about 0.5 wt % to about 2 wt %, such as about 0.8 wt % to about 1.5 wt %, preferably about 1.0 wt % to about 1.2 wt %, with respect to the total weight of said aqueous wound healing formulation.

74. The aqueous wound healing formulation according to any one of clauses 55-73, wherein said aqueous wound healing formulation comprises one or more preservative agents.

75. The aqueous wound healing formulation according to any one of clauses 55-74, wherein said one or more preservative agents are selected from the group consisting of phenoxyethanol, glycerin, methyl-4-hydroxy benzoate, propyl 4-hydroxybenzoate, butyl 4-hydroxybenzoate, triethylene glycol, benzyl alcohol, methylisothiazolinone, methylchloroisothiazolinone, diazolidinyl urea, imidazolidinyl urea, methylparaben, ethylparaben, propylparaben, butylparaben, and isobutylparaben, and combinations thereof.

76. The aqueous wound healing formulation according to any one of clauses 55-75, wherein said one or more preservative agents comprise or consist of phenoxyethanol and/or glycerin.

77. The aqueous wound healing formulation according to any one of clauses 55-76, wherein the total amount of said one or more preservative agents is in the range of about 0.5 wt % to about 2 wt %, such as about 0.7 wt % to about 1.5 wt %, preferably about 0.9 wt % to about 1.1 wt %, with respect to the total weight of said aqueous wound healing formulation.

78. The aqueous wound healing formulation according to any one of clauses 55-77, wherein said aqueous formulation further comprises one or more colouring agents.

79. The aqueous wound healing formulation according to clause 78, wherein said one or more colouring agents are dyes or pigments.

80. The aqueous wound healing formulation according to any one of clauses 78 or 79, wherein said one or more colouring agents are artificial colouring agents or natural colouring agents.

81. The aqueous wound healing formulation according to any one of clauses 78-80, wherein the total amount of said one or more colouring agents is in the range of about 0.1 wt % to about 15 wt %, such as about 1 wt % to about 12 wt %, such as about 2 wt % to about 10 wt %, with respect to the total weight of said aqueous wound healing formulation.

82. The aqueous wound healing formulation according to any one of clauses 55-81, wherein said aqueous wound healing formulation further comprises one or more additives selected from the group consisting of antiseptic agents, local anaesthetic agents, anti-inflammatory agents, antihistamines, and botanical ingredients, and combinations thereof.

83. The aqueous wound healing formulation according to any one of clauses 55-82, wherein said aqueous wound healing formulation further comprises one or more antiseptic agents.

84. The aqueous wound healing formulation according to any one of clauses 82 or 83, wherein said one or more antiseptic agents are selected from the group consisting of benzethonium chloride, chlorhexidine, chloroxylenol, isopropyl alcohol, hexachlorophene, benzalkonium chloride, and hydrogen peroxide, and combinations thereof.

85. The aqueous wound healing formulation according to any one of clauses 82-84, wherein said one or more antiseptic agents comprise or consist of benzethonium chloride.

86. The aqueous wound healing formulation according to any one of clauses 82-85, wherein the total amount of said antiseptic agent in said aqueous formulation is in the range of about 0.1 wt % to about 0.5 wt %, preferably about 0.1 wt % to about 0.3 wt %, with respect to the total weight of said aqueous wound healing formulation.

87. The aqueous wound healing formulation according to any one of clauses 55-86, wherein said aqueous wound healing formulation further comprises one or more local anaesthetic agents.

88. The aqueous wound healing formulation according to clause 87, wherein said one or more local anaesthetic agents are selected from the group consisting of lidocaine, benzocaine, butamben, dibucaine, oxybuprocaine, pramoxine, proxymetacaine, and tetracaine, and combinations thereof.

89. The aqueous wound healing formulation according to any one of clauses 87 or 88, wherein said one or more local anaesthetic agents comprise or consist of lidocaine and/or benzocaine.

90. The aqueous wound healing formulation according to any one of clauses 87-89, wherein the total amount of said one or more local anaesthetic agents is in the range of about 0.1 wt % to about 20 wt %, with respect to the total weight of said aqueous wound healing formulation.

91. The aqueous wound healing formulation according to any one of clauses 55-90, wherein said aqueous wound healing formulation further comprises one or more anti-inflammatory agents.

92. The aqueous wound healing formulation according to clause 91, wherein said one or more anti-inflammatory agents are hormones and/or nonsteroidal anti-inflammatory drugs (NSAIDs).

93. The aqueous wound healing formulation according to any one of clauses 91 or 92, wherein said one or more anti-inflammatory agents comprise or consist of cortisone.

94. The aqueous wound healing formulation according to any one of clauses 91-93, wherein the total amount of said one or more anti-inflammatory is in the range of about 0.1 wt % to about 10 wt %, with respect to the total weight of said aqueous wound healing formulation.

95. The aqueous wound healing formulation according to any one of clauses 55-94, wherein said aqueous wound healing formulation further comprises one or more botanical ingredients.

96. The aqueous wound healing formulation according to clause 95, wherein said one or more botanical ingredients are selected from the group consisting of herbs, roots, flowers, fruits, leaves, and seeds, and combinations thereof.

97. The aqueous wound healing formulation according to any one of clauses 95 or 96, wherein said one or more botanical ingredients are selected from the group consisting of aloe, chamomile, lavender, tea tree oil, calendula, dandelion, and lotus, and combinations thereof.

98. The aqueous wound healing formulation according to any one of clauses 55-97, wherein said aqueous wound healing formulation is substantially free of organic solvents.

99. The aqueous wound healing formulation according to any one of clauses 55-98, wherein said aqueous wound healing formulation is substantially free of alcohol.

100. A container comprising an aqueous wound healing formulation according to any one of clauses 55-99.

101. The container according to clause 100, wherein the container is of a type selected from the group consisting of bottles, spray packs, daubers and droppers.

102. The container according to any one of clauses 100 or 101, wherein the container comprises a means for applying the aqueous wound healing formulation to the skin.

103. The container according to any one of clauses 100-102, wherein the container is a bottle.

104. The container according to clause 103, wherein the bottle comprises a lid comprising an applicator brush.

105. A method for producing an aqueous wound healing formulation according to any one of clauses 55-99, said method comprising the steps of:
(i) providing a mixing container comprising an aqueous solvent,
(ii) adding the first polymer to said mixing container under stirring, and
(iii) adding the second polymer to said mixing container under stirring.

106. The method according to clause 105, further comprising a step of adding a thickening agent to the aqueous solvent before adding said first polymer.

107. The method according to any one of clauses 105 or 106, further comprising a step of adding a preservative to the mixing container after adding said second polymer.

108. An aqueous wound healing formulation according to any one of clauses 55-99 for use as a medicament.

109. An aqueous wound healing formulation according to any one of clauses 55-99 for use in the treatment of a minor injury to the skin.

110. The aqueous wound healing formulation for use according to clause 109, wherein the minor injury to the skin is selected from the group consisting of wounds, cuts, abrasions, burns, blisters, calluses, insect bites and stings.

111. The aqueous wound healing formulation for use according to any one of clauses 109 or 110, wherein said aqueous wound healing formulation is applied topically to the skin.

112. Use of a water-soluble or a water-dispersible polymeric material comprising a first polymer which is a vinyl polymer, and a second polymer which is an acrylic polymer, for preparation of an aqueous wound healing formulation.

113. The use according to clause 112, wherein said vinyl polymer comprises a polyvinyl ester polymer.

114. The use according to clause 113, wherein said polyvinyl ester polymer is selected from the group consisting of polyvinyl acetate (PVAc), polyvinyl benzoate, polyvinyl butyrate, polyvinyl formate, polyvinyl propionate, and polyvinyl stearate.

115. The use according to any one of clauses 112-114, wherein the first polymer comprises polyvinyl acetate.

116. The use according to any one of clauses 112-115, wherein the amount of the first polymer is in the range of about 5 wt % to about 20 wt %, such as about 8 wt % to about 18 wt %, such as about 12 wt % to about 17 wt %, with respect to the total weight of said aqueous wound healing formulation.

117. The use according to any one of clauses 112-116, wherein the acrylic polymer is an acrylate copolymer.

118. The use according to clause 117, wherein said acrylate copolymer comprises styrene or a derivative thereof.

119. The use according to any one of clauses 117 or 118, wherein said acrylate copolymer is a styrene/acrylate copolymer.

120. The use according to any one of clauses 117-119, wherein the weight ratio between the first polymer and second polymer is in the range of about 3.2:1 to about 1:1, such as about 3.2:1 to about 1.5:1.

121. The use according to clause 117, wherein said acrylate copolymer is a copolymer of allyl methacrylate and one or more monomers consisting of acrylic acid and/or methacrylic acid.

122. The use according to clause 121, wherein said acrylate copolymer is a copolymer of allyl methacrylate and an aminomethyl propanol salt of a monomer consisting of acrylic acid and/or methacrylic acid (AMP-acrylate).

123. The use according to any one of clauses 121 or 122, wherein the weight ratio between the first polymer and second polymer is in the range of about 8:1 to about 1:1, such as about 6:1 to about 2:1, such as about 5:1 to about 3:1.

124. The use according to any one of clauses 112-123, wherein said aqueous wound healing formulation does not comprise any cyanoacrylate polymers.

125. The use according to any one of clauses 112-124, wherein said aqueous wound healing formulation is substantially free of organic solvents.

126. The use according to any one of clauses 112-125, wherein said aqueous wound healing formulation is substantially free of alcohol.

127. A kit-of-parts comprising:
(i) an aqueous wound healing formulation according to any one of clauses 55-99 and optionally a means for applying the aqueous wound healing formulation to the skin; or
(ii) a container according to any one of clauses 100-104; and
(iii) instructions for use.

The invention will now be described in further details in the following non-limiting examples.

EXAMPLES

The following polymers were used; Polyvinyl acetate (UltraPure polymer, Ultra Chemical, 55% active polymer in water—CAS #9003-20-7), Styrene/acrylate copolymer (Dermacryl E, Nouryon, 45% active in water, CAS #25767-47-9), AMP-acrylate/Allyl methacrylate copolymer (Fixate G-100 polymer, Lubrizol, 30% active polymer in water). The thickening agent was xanthan gum (Keltrol CG-SFT). The preservative was Euxyl PE 9010 (phenoxyethanol and ethylhexylglycerin; Shulke).

Example 1: Water Resistance and Adhesion of Aqueous Wound Healing Formulation Comprising Different Polymer Material In order for an aqueous wound healing formulation to be effective, it needs to form an aesthetically acceptable film without tackiness, brittleness and with integrity, it must be able to resist unintentional water wash off once dried, and it must have reasonable adhesion to skin. To that effect, films were dried on (i) skin to assess their aesthetic acceptability and (ii) aluminum foil to evaluate their water resistance and film adhesion.

Method:

A range of different aqueous wound healing formulations according to Table 1 were prepared to assess the water resistance and adhesion properties of the resulting protective films. Water was added to a main beaker and mixing was initiated with an overhead propeller blade mixer at 200 rpm. The ingredients were added to the water in sequential steps in the following order; xanthan gum, polymer(s), and preservative. Each sequential step was followed by blending of the mixture until a homogenous mixture was obtained. pH was adjusted to between 5.75 and 6.25 using 20% citric acid or 20% NaOH as necessary, QS with water if needed.

TABLE 1

Composition of aqueous wound healing formulations comprising different polymer material. All ingredients are given as weight percentages (wt %) with respect to the total weight of the formulation.

| INCI name | Exp #1 (wt %) | Exp #2 (wt %) | Exp #3 (wt %) | Exp #4 (wt %) | Exp #5 (wt %) | Exp #6 (wt %) | Exp #7 (wt %) |
|---|---|---|---|---|---|---|---|
| Water | 86.9 | 90.4 | 90.4 | 83.6 | 81.2 | 93.4 | 85.2 |
| Xanthan gum | 1.1 | 1.1 | 1.1 | 1.1 | 1.1 | 1.1 | 1.1 |
| Polyvinyl acetate (PVAC) | 13.8 | — | — | 3.8 | 13.8 | — | 8.25 |
| AMP-acrylate/Allyl methacrylate copolymer | — | 7.5 | — | — | 3.0 | — | — |
| Polyurethane-1 | — | — | 7.5 | 10.5 | — | — | — |
| Styrene/acrylate copolymer | — | — | — | — | — | 4.5 | 4.5 |
| Preservative | 1.0 | 1.0 | 1.0 | 1.0 | 1.0 | 1.0 | 1.0 |

Water resistance and film adhesion was assessed using the following procedure. On a piece of heavy duty aluminum foil, a two-inch by two-inch square was drawn with a marker. 1.5 g of the aqueous wound healing formulation was added onto the aluminum foil, staying within the two-inch by two-inch square. The product was spread as evenly as possible using a brush or the end of a pipette while staying within the two-inch by two-inch square. The film was allowed to dry completely on the aluminum foil for a minimum of 24 hours. Films that adhered to the aluminum foil after four hours without any noticeable detachment were considered to have passed the adhesion test. Once completely dry, the aluminum foil was placed into a 250 mL beaker and 200 g of tap water was added. Over a four-hour period, swelling and detachment (if any) of the film immersed in water was recorded every 5-10 minutes. Films remaining intact over the entirety of the four-hour period were considered to have passed the water resistance test.

Results:

Formulations comprising only singular polymers (Exp #1-3 and Exp #6) resulted in films that did not have proper skin adhesion (Exp #1), did not have good water resistance (Exp #2 and 3) or did not yield an aesthetically acceptable film (Exp #6). When polyvinyl acetate (PVAC) was combined with polyurethane-1 (Exp #4), an aesthetically good film was formed that adhered to skin but did not display sufficient water resistance.

Combinations of PVAC with either AMP-acrylate/allyl methacrylate copolymer (Exp #5) or styrene/acrylate copolymer (Exp #7) yielded an aesthetically good, tough film with good skin adhesion and good water resistance.

Conclusion:

This example demonstrates that aqueous wound healing formulations comprising PVAC and an acrylic polymer yielded protective films with excellent performance.

Example 2: Aqueous Wound Healing Formulations Comprising Polymer Material with Varying Polymer Ratios To investigate the influence on polymer ratio on protective film performance, a range of aqueous wound healing formulations with varying polymer ratios of polyvinyl acetate and AMP-acrylate/Allyl methacrylate copolymer were prepared and assessed. Film aesthetics, adhesion and water resistance were evaluated as described in Example 1.

Method:

Aqueous wound healing formulations were prepared according to Table 2 following the same method as in Example 1. Water was added to a main beaker and mixing was initiated with an overhead propeller blade mixer at 200 rpm. The ingredients were added to the water in sequential steps in the following order; xanthan gum, PVAC, AMP-acrylate/Allyl methacrylate copolymer, and preservative. Each sequential step was followed by blending of the mixture until a homogenous mixture was obtained, followed by pH adjustment as described in Example 1 above as necessary.

TABLE 2

Composition of aqueous wound healing formulations comprising different ratios and quantities of PVAC and AMP-acrylate/Allyl methacrylate copolymer. All ingredients are given as weight percentages (wt %) with respect to the total weight of the formulation.

| INCI name | Exp #8 (wt %) | Exp #9 (wt %) | Exp #10 (wt %) | Exp #11 (wt %) |
|---|---|---|---|---|
| Water | 81.1 | 79.5 | 77.8 | 76.1 |
| Xanthan gum | 1.1 | 1.1 | 1.1 | 1.1 |
| Polyvinyl acetate (PVAC) | 13.8 | 15.1 | 16.5 | 17.9 |
| AMP-acrylate/Allyl methacrylate copolymer | 3.0 | 3.3 | 3.6 | 3.9 |
| Preservative | 1.0 | 1.0 | 1.0 | 1.0 |

Results:

All experiments (Exp #8-11) yielded tough films with good skin adhesion and excellent water resistance. Films with the higher polymer content (Exp #11) formed the toughest, most durable films.

Conclusion:

This example demonstrates that a range of aqueous wound healing formulations comprising varying ratios of polymers are suitable for forming protective films with excellent performance.

Example 3: Aqueous Wound Healing Formulations Comprising Antiseptic Agent

To test the influence of including further additives in the aqueous wound healing formulation on film formation, formulations comprising benzethonium chloride, mica and titanium dioxide were prepared and evaluated (Table 3). The formulations were prepared with varying polymer ratios of polyvinyl acetate and styrene/acrylate copolymer.

Moreover, aqueous wound healing formulation with a fixed total polymer content but varying polymer ratios (Table 4) were tested to identify favourable ratios of polymers.

Method:

Aqueous wound healing formulations comprising an antiseptic agent were prepared according to Table 3 below. Water was added to a main beaker and mixing was initiated with an overhead propeller blade mixer at 200 rpm. The ingredients were added to the water in sequential steps in the following order; xanthan gum, PVAC, styrene/acrylate copolymer, mica, titanium dioxide, and preservative. Each sequential step was followed by blending of the mixture until a homogenous mixture was obtained, followed by pH adjustment as described in Example 1 above as necessary. The water resistance and adhesion properties of the resulting protective films were evaluated as described in Example 1.

TABLE 3

Composition of aqueous wound healing formulations comprising antiseptic agent. All ingredients are given as weight percentages (wt %) with respect to the total weight of the formulation.

| INCI name | Exp #12 (wt %) | Exp #13 (wt %) | Exp #14 (wt %) | Exp #15 (wt %) | Exp #16 (wt %) |
| --- | --- | --- | --- | --- | --- |
| Water | 67.8 | 72.3 | 70.95 | 76.95 | 79.1 |
| Xanthan gum | 1.1 | 1.1 | 1.1 | 1.1 | 1.1 |
| Polyvinyl acetate | 16.5 | 16.5 | 16.5 | 8.25 | 3.85 |
| Styrene/acrylates copolymer | 5.4 | 0.9 | 2.25 | 4.5 | 6.75 |
| Mica | 7 | 7 | 7 | 7 | 7 |
| Titanium dioxide | 1 | 1 | 1 | 1 | 1 |
| Benzethonium chloride | 0.2 | 0.2 | 0.2 | 0.2 | 0.2 |
| Preservative | 1.0 | 1.0 | 1.0 | 1.0 | 1.0 |

Aqueous wound healing formulations with a total polymer content 19.5 wt % were prepared according to Table 4 below. Water was added to a main beaker and mixing was initiated with an overhead propeller blade mixer at 200 rpm. The ingredients were added to the water in sequential steps in the following order; propylene glycol, xanthan gum, PVAC, styrene/acrylate copolymer, mica, titanium dioxide, and preservative. Each sequential step was followed by blending of the mixture until a homogenous mixture was obtained. The water resistance and adhesion properties of the resulting protective films were evaluated as described in Example 1.

TABLE 4

Composition of aqueous wound healing formulation with a total polymer content of 19.5 wt %. All ingredients are given as weight percentages (wt %) with respect to the total weight of the formulation.

| INCI name | Exp #17 (wt %) | Exp #18 (wt %) | Exp #19 (wt %) |
| --- | --- | --- | --- |
| Water | 69.63 | 69.775 | 69.8 |
| Xanthan gum | 1.1 | 1.1 | 1.1 |
| Propylene glycol | 0.5 | 0.5 | 0.5 |
| Polyvinyl acetate | 15.0 | 14.1 | 12.7 |
| Styrene/acrylate copolymer | 4.5 | 5.4 | 6.8 |
| Mica | 7.0 | 7.0 | 7.0 |
| Titanium dioxide | 1 | 1 | 1 |
| Benzethonium chloride | 0.2 | 0.2 | 0.2 |
| Preservative | 1.0 | 1.0 | 1.0 |

Results:

Exp #12-15 yielded aesthetically good films, whereas exp #16 exhibited a brittle, unaesthetically appealing protective film. While the protective films of exp #13 and 14 had acceptable aesthetics on dry down, they did not exhibit sufficient adherence and water resistance. Protective films that passed all three criteria (aesthetics, water resistance and adhesion) included exp #12 and 15.

Exp #17 failed to achieve an acceptable water resistance and adhesion level. Exp #18 and 19 on the other hand yielded protective films with good aesthetics as well as sufficient adhesion and water resistance.

Conclusion:

This example demonstrates that a minimum content of both PVAC and styrene/acrylate copolymer is advantageous to achieve protective films with desirable properties.

Additionally, this example demonstrates that the ratio of PVAC to styrene/acrylate copolymer preferably does not exceed 3:1.

Example 4: Further Aqueous Wound Healing Formulations

Aqueous wound healing formulations were prepared according to Table 5 below following essentially the same method as in Example 1 above. To provide a homogenous mixture, followed by pH adjustment to between 6.0 and 6.5 using citric acid and/or NaOH as described in Example 1 above and as necessary. The colouring agents manganese violet and isopropyl titanium triisostearate (BMV-12; Kobo) and titanium dioxide and isopropyl titanium triisostearate (RBTD-12; Kobo) were also used in one of the formulations.

TABLE 5

Composition of aqueous wound healing formulations. All ingredients are given as weight percentages (wt %) with respect to the total weight of the formulation.

| INCI name | Exp #20 (wt %) | Exp #21 (wt %) |
| --- | --- | --- |
| Water | 78.4 | 68.6 |
| Xanthan gum | 1.1 | 1.1 |
| Polyvinyl acetate | 12.7 | 12.7 |
| Styrene/acrylate copolymer | 6.8 | 6.8 |
| Manganese violet and isopropyl titanium triisostearate | — | 9.0 |
| Titanium dioxide and isopropyl titanium triisostearate | — | 0.8 |
| Preservative | 1.0 | 1.0 |

Example 5: Product Study Among Users

The utility of the aqueous wound healing formulations was evaluated by subjecting a representative formulation to an end-user trial and survey.

Method:

An aqueous wound healing formulation according with a composition described in Table 6 below and prepared essentially as described in Example 1 above was dispatched to a test panel containing 102 respondents.

TABLE 6

Composition of aqueous wound healing formulation used in trial. All ingredients are given as weight percentages (wt %) with respect to the total weight of the formulation.

| INCI name | Exp #22 (wt %) |
|---|---|
| Water | 68.0 |
| Xanthan gum | 1.1 |
| Polyvinyl acetate and water | 16.5 |
| AMP-acrylate/Allyl methacrylate copolymer | 3.6 |
| Manganese violet and isopropyl titanium triisostearate | 9.0 |
| Titanium dioxide and isopropyl titanium triisostearate | 0.8 |
| Preservative | 1.0 |

The respondents were parents to one or more children of age 2-12 years. Within the testing period, the respondents on average tested the aqueous wound healing formulation 2.5 times on themselves and 3.0 times on their children. Most of the times the formulation was applied to an actual cut or scrape. The test panel data is collated in Table 7. After the end of the trial period the respondents answered a questionnaire to evaluate the aqueous wound healing formulation.

TABLE 7

Test panel data and usage information.

| Usage | Used on self | Used on child |
|---|---|---|
| Number of times formulation was used | | |
| Mean number (#) | 2.5 | 3.0 |
| How the formulation was used | | |
| On an actual cut/scrape (%) | 63 | 75 |
| Just to try the formulation on (%) | 37 | 25 |
| Age distribution of children test panel | | |

| Age of child | Respondents that used on child (%) |
|---|---|
| 2-4 years | 32 |
| 5-7 years | 41 |
| 8-12 years | 52 |

Results:

The answers from the respondents to the questionnaire following up on the trial period are summarised in Table 8 below.

Summary of the respondents' evaluation after the trial period.

Key measure performance

| Metric | Respondents' evaluation |
|---|---|
| Formulation solves problem | 83% - "extreme well" or "very well" |
| Effectiveness of formulation | 81% - "extremely effective" or "very effective" |
| Problems with formulation | 92% - "no problems" |
| Feeling on skin | 93% - "like a lot" or "like a little" |
| Liking of the formulation (respondents) | 89% - "very much" or "somewhat" |
| Liking of the formulation (children) | 92% - "very much" or "somewhat" |
| Buying propensity | 87% - "definitely" or "probably" |

Summary of the respondents' evaluation after the trial period.

Product imagery after trial

| Question | Respondents answered "agree completely" or "agree very much" |
|---|---|
| Is easy to apply | 94% |
| Does not hurt when applying | 88% |
| Does not hurt when removing | 87% |
| Is easy to remove | 86% |
| Keeps cuts clean | 82% |
| Prevents infections | 76% |
| Dries quickly | 71% |

Satisfaction with formulation

| Metric | Respondents answered "extremely satisfied" or "very satisfied" |
|---|---|
| Application | 90% |
| Removal | 85% |
| Sealing (out water and germs) | 82% |
| Length of time it stayed on | 79% |
| Healing | 77% |
| Durability | 77% |
| Drying time | 70% |

Conclusion:

The end-users provided a very positive evaluation of the aqueous wound healing formulation and validated the excellent performance of the formulation.

The invention claimed is:

1. A method of treatment of a minor injury to the skin, which method comprises topically applying to said injured area an aqueous formulation comprising a water-soluble or a water-dispersible polymeric material, which polymeric material is capable of:

(i) adhering to the skin; and (ii) acting as a barrier to moisture but not to oxygen, to cover said injured area, and then allowing water within the aqueous formulation to evaporate to leave a film comprising said polymeric material that covers said injured area, to treat said minor injury;

wherein said aqueous formulation is an aqueous solution of said polymeric material comprising a combination of at least:

a first polymer comprising a polyvinyl ester polymer selected from the group consisting of polyvinyl acetate (PVAc), polyvinyl benzoate, polyvinyl butyrate, polyvinyl formate, polyvinyl propionate, and polyvinyl stearate; and a second polymer comprising a styrene/acrylate copolymer; and wherein the weight ratio between the first polymer and the second polymer is in the range of about 3.2:1 to about 1:1.

2. The method of treatment according to claim 1, wherein, when said water within the aqueous formulation evaporates to leave said film comprising said polymeric material, said film:

(i) covers and adheres to said injured area;

(ii) acts as a barrier to moisture; and (iii) does not act as a barrier to oxygen.

3. The method of treatment according to claim 1, which method comprises providing said aqueous formulation along with instructions to an end user to carry out the method according to claim 1, and wherein the method and/or instructions comprises the additional step(s) of:
- (i) removing the film comprising the polymeric material by washing with water, as required; and/or
- (ii) repeating the method defined in claim 1, as required.

4. The method of treatment according to claim 1, wherein the minor injury to the skin is selected from the group consisting of wounds, cuts, abrasions, burns, blisters, calluses, insect bites and stings.

5. The method of treatment according to claim 1, wherein the amount of the first polymer is in the range of about 5 wt % to about 20 wt % with respect to the total weight of said aqueous formulation.

6. The method of treatment according to claim 1, wherein the weight ratio between the first polymer and the second polymer is in the range of about 3.2:1 to about 1.5:1.

7. The method of treatment according to claim 1, wherein said aqueous formulation does not comprise any cyanoacrylate polymers.

8. The method of treatment according to claim 1, wherein said aqueous formulation further comprises:
- (i) one or more thickening agents selected from the group consisting of cellulosics, gums, saccharides, proteins, organosilicones, and fumed silica, and combinations thereof;
- (ii) one or more preservative agents selected from the group consisting of phenoxyethanol, glycerin, methyl-4-hydroxy benzoate, propyl 4-hydroxybenzoate, butyl 4-hydroxybenzoate, triethylene glycol, benzyl alcohol, methylisothiazolinone, methylchloroisothiazolinone, diazolidinyl urea, imidazolidinyl urea, methylparaben, ethylparaben, propylparaben, butylparaben, and isobutylparaben, and combinations thereof;
- (iii) one or more colouring agents, wherein said one or more colouring agents are dyes or pigments selected from artificial colouring agents or natural colouring agents; and/or
- (iv) one or more additives selected from the group consisting of:
  - a. antiseptic agents selected from the group consisting of benzethonium chloride, chlorhexidine, chloroxylenol, isopropyl alcohol, hexachlorophene, benzalkonium chloride, and hydrogen peroxide;
  - b. local anaesthetic agents selected from the group consisting of lidocaine, benzocaine, butamben, dibucaine, oxybuprocaine, pramoxine, proxymetacaine, and tetracaine;
  - c. anti-inflammatory agents selected from hormones and/or nonsteroidal anti-inflammatory drugs (NSAIDs);
  - d. antihistamines;
  - e. botanical ingredients selected from the group consisting of herbs, roots, flowers, fruits, leaves, and seeds,
  and combinations thereof.

9. The method of treatment according to claim 8, wherein said one or more thickening agents comprises a gum selected from the group consisting of xanthan, guar, cellulose, locust bean, and acacia, and combinations thereof.

10. The method of treatment according to claim 8, wherein the total amount of said one or more thickening agents in said aqueous formulation is in the range of about 0.5 wt % to about 2 wt % with respect to the total weight of said aqueous formulation.

11. The method of treatment according to claim 8, wherein the total amount of said one or more preservative agents in said aqueous formulation is in the range of about 0.5 wt % to about 2 wt % with respect to the total weight of said aqueous formulation.

12. The method of treatment according to claim 8, wherein the total amount of said one or more colouring agents in said aqueous formulation is in the range of about 0.1 wt % to about 15 wt % with respect to the total weight of said aqueous formulation.

13. The method of treatment according to claim 8, wherein said one or more antiseptic agents comprise or consist of benzethonium chloride.

14. The method of treatment according to claim 8, wherein the total amount of said one or more antiseptic agents in said aqueous formulation is in the range of about 0.1 wt % to about 0.5 wt % with respect to the total weight of said aqueous formulation.

15. The method of treatment according to claim 8, wherein said one or more local anaesthetic agents comprise or consist of lidocaine and/or benzocaine.

16. The method of treatment according to claim 8, wherein the total amount of said one or more local anaesthetic agents in said aqueous formulation is in the range of about 0.1 wt % to about 20 wt %, with respect to the total weight of said aqueous formulation.

17. The method of treatment according to claim 8, wherein said one or more anti-inflammatory agents comprise or consist of cortisone.

18. The method of treatment according to claim 8, wherein the total amount of said one or more anti-inflammatory agents in said aqueous formulation is in the range of about 0.1 wt % to about 10 wt %, with respect to the total weight of said aqueous formulation.

19. The method of treatment according to claim 8, wherein said one or more botanical ingredients are selected from the group consisting of aloe, chamomile, lavender, tea tree oil, calendula, dandelion, and lotus, and combinations thereof.

20. The method of treatment according to claim 1, wherein said aqueous formulation is substantially free of organic solvents and/or is substantially free of alcohol.

21. The method of treatment according to claim 1, wherein said film is at least about 50% impermeable to ingress of water through the polymer film, and/or at least about 10% permeable to air/oxygen.

22. The method of treatment according to claim 1, wherein the aqueous formulation is provided in a container of a type selected from the group consisting of bottles, spray packs, daubers and droppers.

23. The method of treatment according to claim 22, wherein the container comprises a means for applying the aqueous formulation to the skin.

24. The method of treatment according to claim 22, wherein the container is a bottle and/or comprises a lid comprising an applicator brush.

* * * * *